(12) United States Patent
Esterberg

(10) Patent No.: US 12,390,281 B2
(45) Date of Patent: Aug. 19, 2025

(54) SYSTEMS AND METHODS FOR ASSISTED SURGICAL NAVIGATION

(71) Applicant: GLOBUS MEDICAL, INC., Audubon, PA (US)

(72) Inventor: Justin Esterberg, Mercer Island, WA (US)

(73) Assignee: Globus Medical, Inc., Audubon, PA (US)

( * ) Notice: Subject to any disclaimer, the term of this patent is extended or adjusted under 35 U.S.C. 154(b) by 266 days.

(21) Appl. No.: 17/380,125

(22) Filed: Jul. 20, 2021

(65) Prior Publication Data
US 2021/0346102 A1     Nov. 11, 2021

Related U.S. Application Data

(63) Continuation of application No. 16/001,055, filed on Jun. 6, 2018, now Pat. No. 11,083,527, which is a
(Continued)

(51) Int. Cl.
*A61B 34/20*     (2016.01)
*A61B 5/055*     (2006.01)
(Continued)

(52) U.S. Cl.
CPC ............ *A61B 34/20* (2016.02); *A61B 5/055* (2013.01); *A61B 34/10* (2016.02); *G06F 3/011* (2013.01);
(Continued)

(58) Field of Classification Search
CPC .......... G02B 27/0172; G02B 2027/014; G02B 2027/0134; G02B 2027/0138; H04N 13/239; A61B 34/10; A61B 2034/2065; A61B 2090/371; A61B 1/00; A61B 2034/2057; A61B 34/20; A61B 5/055; A61B 90/98; A61B 2017/00207; A61B 2034/107; A61B 2034/2048; A61B 2034/2051; A61B 2034/2055; A61B 2034/2063; A61B 2034/2072; A61B 2090/309; A61B 2090/365;
(Continued)

(56) References Cited

U.S. PATENT DOCUMENTS

| 5,933,457 A * | 8/1999 | Hottinen ............ H04B 1/71052 375/349 |
| 6,246,900 B1 * | 6/2001 | Cosman ................ A61B 34/20 606/130 |

(Continued)

*Primary Examiner* — William Lu

(57) ABSTRACT

In at least one embodiment, a method of surgical navigation is provided. The method includes receiving an external three-dimensional model of a surgical site from the viewpoint of a headset, wherein the external three-dimensional model is derived from reflected light. The method further includes aligning the external three-dimensional model with an internal three-dimensional model of the surgical site from the viewpoint of the headset, wherein the internal three-dimensional model is derived from medical imaging, and generating an aligned view. The method further includes providing the aligned view to the headset, and updating the aligned view in real-time while the headset is moved or the surgical site is moved or modified during a surgical procedure.

11 Claims, 31 Drawing Sheets

Related U.S. Application Data continuation of application No. 15/291,357, filed on Oct. 12, 2016, now Pat. No. 10,016,243, which is a continuation of application No. 14/999,070, filed on Mar. 28, 2016, now abandoned.

(60) Provisional application No. 62/136,877, filed on Mar. 23, 2015.

(51) Int. Cl.

| *A61B 17/00* | (2006.01) |
|---|---|
| *A61B 34/10* | (2016.01) |
| *A61B 90/00* | (2016.01) |
| *A61B 90/30* | (2016.01) |
| *A61B 90/50* | (2016.01) |
| *A61B 90/98* | (2016.01) |
| *G06F 3/01* | (2006.01) |

(52) U.S. Cl.
CPC .............. *A61B 2017/00207* (2013.01); *A61B 2034/107* (2016.02); *A61B 2034/2048* (2016.02); *A61B 2034/2051* (2016.02); *A61B 2034/2055* (2016.02); *A61B 2034/2063* (2016.02); *A61B 2034/2065* (2016.02); *A61B 2034/2072* (2016.02); *A61B 2090/309* (2016.02); *A61B 2090/365* (2016.02); *A61B 2090/371* (2016.02); *A61B 2090/372* (2016.02); *A61B 2090/373* (2016.02); *A61B 2090/502* (2016.02); *A61B 90/98* (2016.02); *A61B 2560/0487* (2013.01)

(58) Field of Classification Search
CPC ........ A61B 2090/372; A61B 2090/373; A61B 2090/502; A61B 2560/0487; G06F 2203/04804; G06F 3/011; G16Z 99/00; G06T 2210/41
See application file for complete search history.

(56) References Cited

U.S. PATENT DOCUMENTS

| 9,550,029 | B2* | 1/2017 | Boyden | A61B 90/11 |
|---|---|---|---|---|
| 10,016,243 | B2* | 7/2018 | Esterberg | G06F 3/011 |
| 10,046,119 | B2* | 8/2018 | Boyden | A61B 90/11 |
| 10,911,677 | B1* | 2/2021 | Zhou | H04N 23/90 |
| 11,049,277 | B1* | 6/2021 | Price | H04N 13/128 |
| 2005/0203380 | A1* | 9/2005 | Sauer | G02B 7/002 |
| | | | | 600/417 |
| 2006/0061660 | A1* | 3/2006 | Brackmann | H04N 23/68 |
| | | | | 348/208.1 |
| 2008/0033410 | A1* | 2/2008 | Rastegar | A61B 34/30 |
| | | | | 606/9 |
| 2011/0275932 | A1* | 11/2011 | Leblond | A61B 5/0062 |
| | | | | 600/425 |
| 2012/0116548 | A1* | 5/2012 | Goree | A61B 5/7253 |
| | | | | 700/90 |
| 2012/0249587 | A1* | 10/2012 | Anderson | G06F 3/04895 |
| | | | | 345/633 |
| 2012/0325003 | A1* | 12/2012 | Berger | A61B 5/0095 |
| | | | | 356/614 |
| 2013/0237811 | A1* | 9/2013 | Mihailescu | A61B 34/20 |
| | | | | 600/407 |
| 2013/0258832 | A1* | 10/2013 | Serr | G11B 7/24044 |
| | | | | 369/103 |
| 2014/0022283 | A1* | 1/2014 | Chan | H04N 9/3185 |
| | | | | 345/633 |
| 2014/0121637 | A1* | 5/2014 | Boyden | A61M 5/427 |
| | | | | 604/116 |
| 2014/0160035 | A1* | 6/2014 | Sauer | G06F 3/041 |
| | | | | 345/173 |
| 2014/0200621 | A1* | 7/2014 | Malackowski | A61B 34/70 |
| | | | | 606/86 R |
| 2015/0173846 | A1* | 6/2015 | Schneider | A61B 1/00042 |
| | | | | 600/424 |
| 2016/0166333 | A1* | 6/2016 | Wang | A61B 34/10 |
| | | | | 600/476 |
| 2016/0191887 | A1* | 6/2016 | Casas | A61B 34/20 |
| | | | | 348/47 |
| 2016/0324580 | A1* | 11/2016 | Esterberg | A61B 34/10 |
| 2017/0143442 | A1* | 5/2017 | Tesar | H04N 23/63 |
| 2017/0259013 | A1* | 9/2017 | Boyden | G16H 30/40 |
| 2017/0318235 | A1* | 11/2017 | Schneider | H04N 5/2628 |
| 2018/0157045 | A1* | 6/2018 | Davami | G02B 27/0172 |
| 2019/0142524 | A1* | 5/2019 | Hladio | G06T 7/30 |
| | | | | 600/249 |
| 2019/0155033 | A1* | 5/2019 | Gelman | G02B 27/0093 |
| 2021/0382559 | A1* | 12/2021 | Segev | G06F 3/013 |

* cited by examiner

LUMBAR SPINE
SHOWING
VIRTUAL 3D FUSION
OF CT MODEL IN ANATOMICAL
REGISTRATION WITH EXTERNAL LANDMARKS (SURGICAL FIELD)

Fig. 6
STEP 1
STEP 2
STEP 3
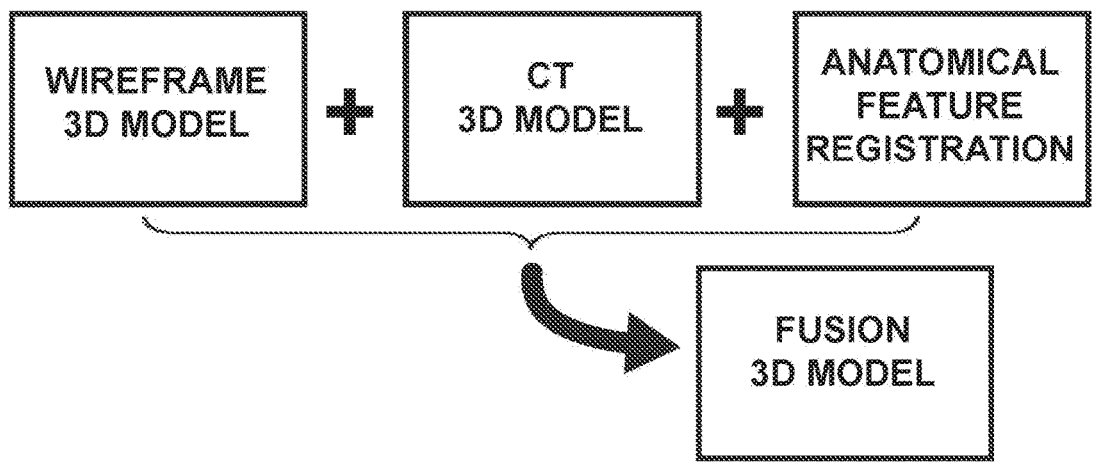
STEP 4

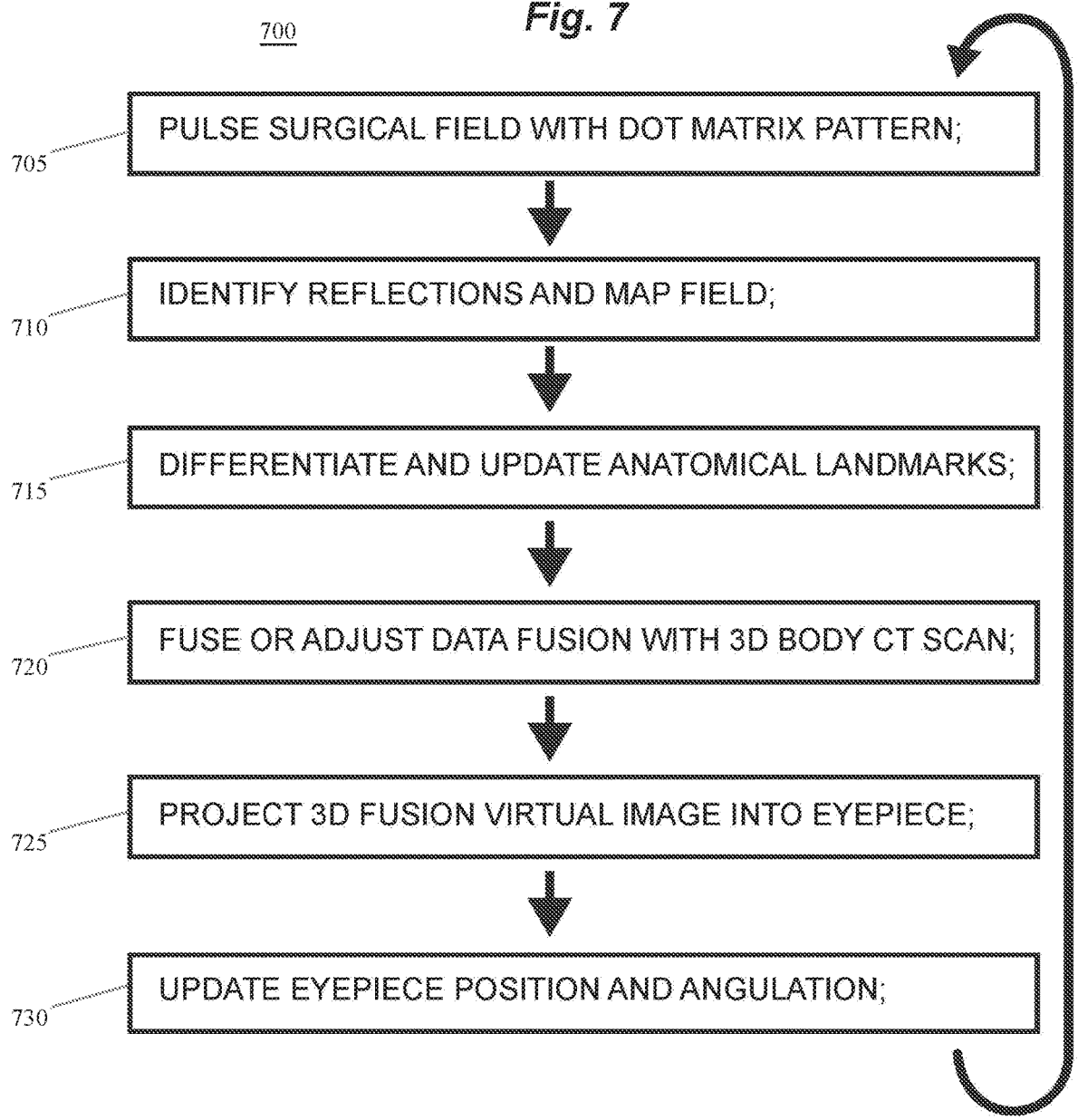

*UMBILICAL*

DOT SUBARRAY (WITH CENTER DOT)

1000

STRUCTURED DOT ARRAY
1100

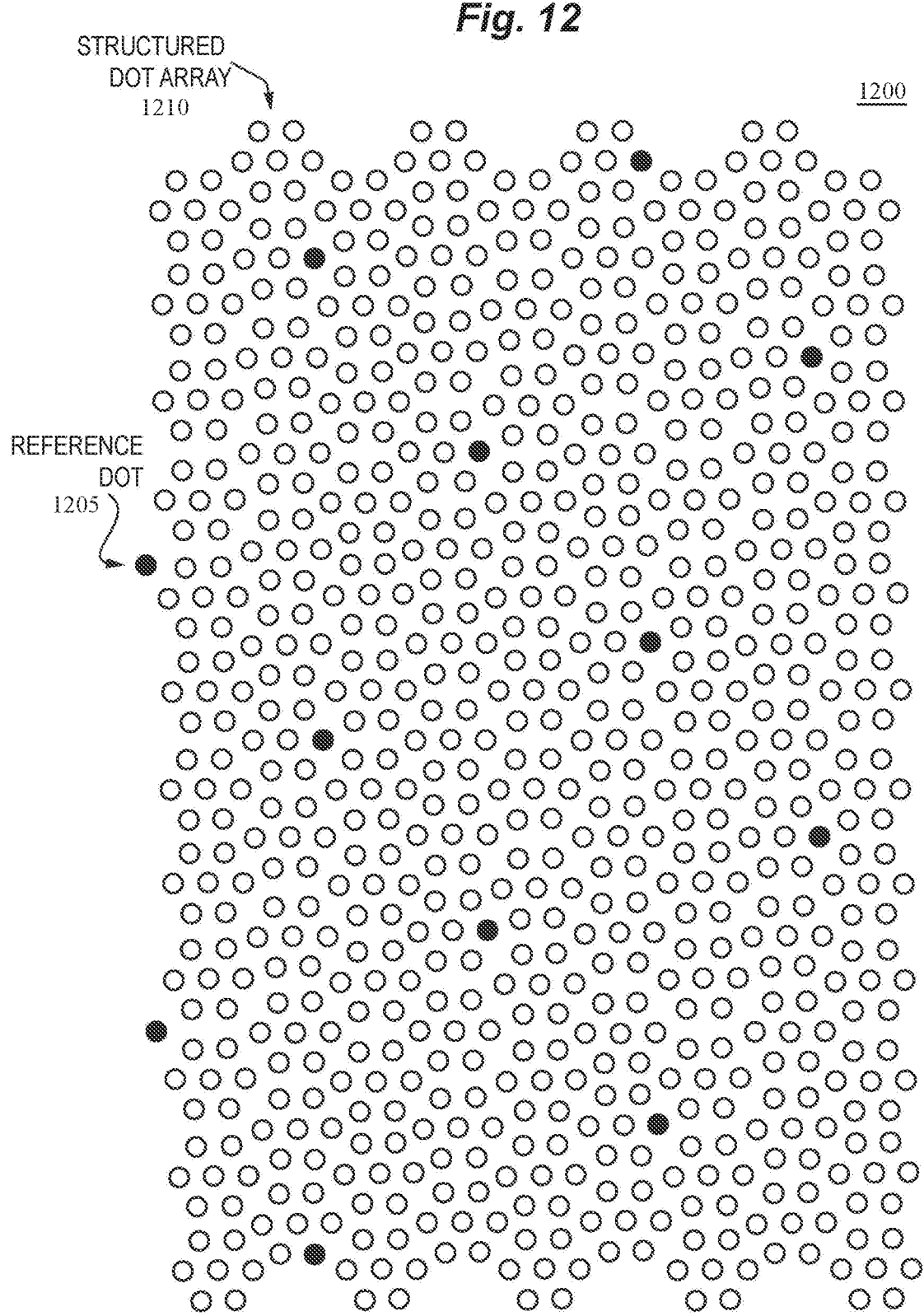

INITIAL SNAP WIREFRAME
1300

FINE MAPPING TERTIARY WIREFRAME
1305

SPREADING ITERATIVE SOLUTION

STEP 1
*Fig. 16A*
1600
STEP 2
STEP 3
STEP 4
AB
| Fig. 16A | Fig. 16B |

Fig. 16B
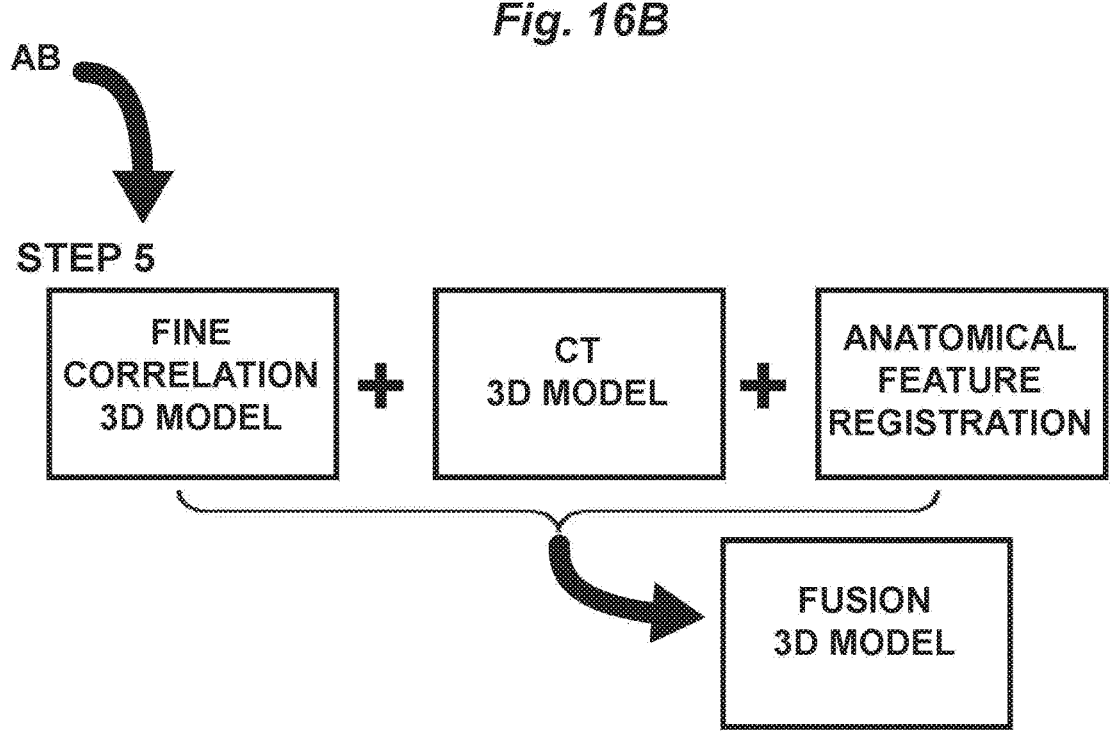
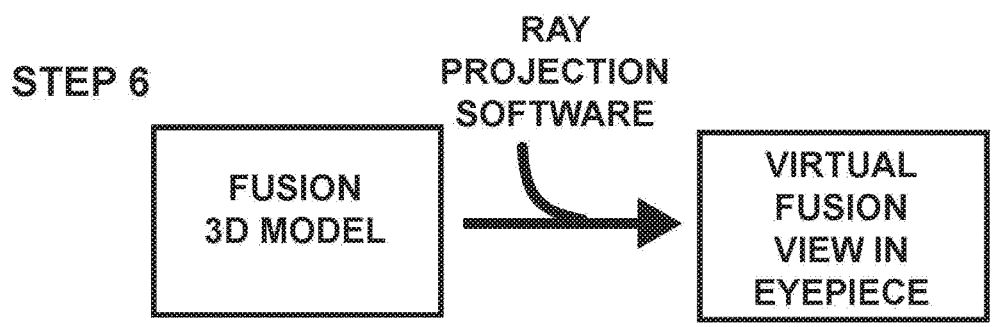
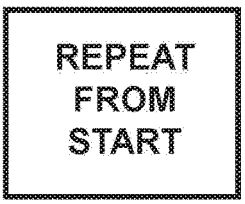
| Fig. 16A | Fig. 16B |

Fig. 19
EYEPIECE VIEW
1900
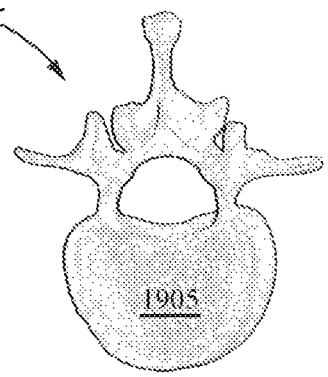
LEVITATE
1905

UNAIDED EYE
2500

GLOVED HANDS

EYEPIECE VIEW

DUPLEX SEGMENTATION
OF TWO VERTEBRAE

COMBINED UNAIDED EYE AND EYEPIECE VIEW
2700

VIRTUAL VIEW FROM VENTRAL SIDE,
RIBS NOT SHOWN FOR CLARITY

SYSTEMS AND METHODS FOR ASSISTED SURGICAL NAVIGATION

CROSS-REFERENCES TO RELATED APPLICATIONS

This application is a divisional application of U.S. patent application Ser. No. 16/001,055, filed on Jun. 6, 2018, which is a continuation of U.S. application Ser. No. 15/291,357, filed Oct. 12, 2016, which is a continuation of U.S. application Ser. No. 14/999,070, filed Mar. 28, 2016, which claims the benefit of U.S. Provisional Application No. 62/136,877, filed Mar. 23, 2015, which are hereby incorporated by reference.

TECHNICAL FIELD

The embodiments described herein relate generally to systems and methods for computer-assisted surgical navigation.

BACKGROUND

Computer-assisted surgical navigation is at the threshold of a revolution in surgery by extending the surgeon's capacity to visualize the underlying anatomy and by guiding positioning of instruments. A variety of innovations in computerized virtual image collection, analysis, fusion and generation are driving these advances. Advances have been made in gaming hardware, military hardware, and augmented reality by which direct pupillary projection is realized of images containing a combination of a camera view and a virtual construct or constructs. Increased numbers of procedures, such as implant placement in the hip and knee, can benefit from precise surgical navigation during the implantation. Improvements in outcomes, as by reduction in the number of revisions because of a misaligned implant, for example, would save more than enough to warrant further investment in improved surgical navigation technologies.

For example, as known in the gaming arts, a physical motion sensor (typically a three-axis accelerometer or gyrosensor, more generally "inertial sensors") can be combined with a camera and display, enabling a first person perspective through a visual window into a virtual space on a display, as is described in U.S. Pat. No. 8,913,009 to Nintendo. Relative spatiality is achieved by defining a stationary window. Thus for example, a player may swing an actuator through the air in a virtual golf game, causing a virtual ball represented on a viewing screen to fly as if struck. Representative patent literature describing the workings of this technology includes U.S. Pat. Doc. Nos. 2012/0258796 and 8100769 to Nintendo, U.S. Pat. Nos. 6,285,379 and 8,537,231 to Philips, and related art for interactive virtual modeling hardware and software such as U.S. Pat. Doc. Nos. 2005/0026703 to Fukawa, 2009/0305785 to Microsoft, and U.S. Pat. Nos. 7,705,830 to Apple and 7,696,980 to Logitech, which disclose technologies for dispensing with keyboards in favor of haptic gesture sets and resultant representation and control of interactive processes. Depth modeling of physical objects using a structured pattern of dots generated by infrared emitters is described in U.S. Pat. Doc. No. 2014/0016113 to Microsoft and in U.S. Pat. No. 6,891,518 to Siemens.

Surgical use is known in the art. U.S. Pat. Nos. 6,787,750 and 6,919,867 to Siemens describe use of optical fiducials to measure depth and location in a surgery. In U.S. Pat. No. 6,919,867, an example is given (Col 4, line 8-Col 6 Line 42) where a surgeon is provided with a view of internal anatomical structures through a head-mounted display while operating. A correct anatomical orientation relative to the patient's body is achieved by mounting retroreflective optical beacons on the patient and around in the workspace and by employing image analysis to identify the location of the beacons. Computing means are taught for relating a coordinate system associated with the camera with a coordinate system relative to the patient's body and for tracking the camera as it moves with the head of the surgeon. However, after almost two decades of development, the resultant systems utilize cumbersome retroreflective balls that must be fastened to bones and surgical tools so that their positions can be mapped, and any images in the headset display appear superimposed on near-field elements such as the surgeon's hands, defeating the surgeon's hand-eye coordination. As a result, most surgeons have reverted to display of the virtual images on a remote display that is accessed by looking up and away from the surgical site.

Infrared markers have also been used for dental surgery (Hassfeld, S et al. 1995. Intraoperative navigation in oral and maxillofacial surgery. Intl J Oral Max Surg 24:111-19). Correlation between CT and patient skin surfaces for guiding surgical procedures was achieved using a laser scanning system (Marmulla R and Niederdellman H. 1998. Computer-assisted bone navigation. J. Craniomaxillofac Surg 26:347-59) and later by the same group (Markerless laser registration in image-guided oral and maxillofacial surgery, J Oral Maxillofac Surg 62:845-51). However, these systems required immobilization of the patient in a reference frame device and again use a remote display to present the image synthesis so as to avoid visual illusions that are paradoxical and confusing.

All these systems rely on optical image analysis that depends on camera frame grabbers that are inoperable and blind when a needed line of sight is blocked. Optical systems are not operative when lighting is insufficient or a direct optical path to the target is obstructed or unrecognizable, such as when smeared with blood or when a surgeon's hands or a surgical instrument is blocking the view from the camera. Image analysis to recognize and triangulate optical fiducials is also computationally intensive, which can be slow or halting, and has the effect of limiting the availability of computer assisted surgical navigation systems by driving up the price and increasing system complexity.

Early computer-aided operating systems include HipNav, OrthoPilot and Praxim. Technologies of relevance have been developed by Simbionix, 3D Systems, BlueBelt Technologies, Medtronic and Siemens. But disadvantages of computer-assisted surgery remain. A major disadvantage is cost, which is generally prohibitive for many hospitals and surgery centers. Improvements have added to the cost, not reduced it. The size of the systems is also disadvantageous. Large C-arms or O-arms and windows take up space in the surgical suite, an important disadvantage in already crowded operating rooms of modern hospitals or clinics in that the equipment becomes a liability when fast action is needed and access is impaired. Additionally, another disadvantage of most surgical navigation systems in current use is the need for intraoperative computerized tomography (CT) imaging, which exposes the patient and staff to significant doses of ionizing radiation.

As applied to surgery, conventional systems generally use a collection of retroreflective spheres that serve as fiducial markers. Clusters of spheres are attached to surgical instruments so that orientation and depth can be monitored using cameras. A pattern of infrared dots is projected onto the surgical field and analysis of the centroid of each dot on spherical surface permits acquisition of the position of each fiducial. Each surgical instrument must include at least four fiducial markers for complete orientational mapping and the needed resolution of the centroids requires a fairly large tetrahedral cluster be used. Fiducial clusters may also be attached to the patient, such as by clipping the marker to an exposed bone. These reflective spheres are not useful, of course, if the optical path is blocked, as occurs frequently in surgery during the more invasive parts of the procedures.

Optics for infrared wavelengths rely on illumination outside the range of human vision, and hence have been adopted as a foundational technology. However, the technology may be better suited to inanimate objects rather than warm bodies. Dichroic mirrors and bandpass filters will not readily separate broadly emitting objects in the 700 to 1200 nm range. Surgical lamps, reflections of hot bulbs off chrome steel, and tools such as cauterizing tips may cause spurious images and add to computation time.

Binocular visors are known in the art and may be used in place of a remote display screen. However, by blinding the surgeon to all but camera generated views, the surgeon can be no more perceptive than the capacity of the system to generate a lifelike display in the visor. Surgeons wishing to rely on an unaided eye and their own hands to perform the procedure must remove the visor. The difficulty of this unsolved problem is underlined in recent literature reports (Bichlmeier C and N Navab, Virtual window for improved depth perception in medical AR; Blum T et al. 2012 Mirracle: an augmented reality magic mirror system for anatomy education. IEEE Virtual Reality).

Moreover, a difficult challenge has not been solved, that of presenting the fusion data as a virtual image that appears as the surgeon would see it in first-person perspective, dynamic and moving with the position of the physician's head and eyes so as to have a believable sense of depth, where the skin and the surgeon's hands are superimposed above the deeper structures. Advantageously, the view would appear as if the surgeon was provided with the capacity to look beneath the skin or surgical field and see underlying boney and visceral structures beneath. The surgical navigation tool would take on a compact and wearable format, such as a monocular eyepiece affixed to a headset worn to the operating room by the surgeon. In order to use this as an interactive intraoperative technique, a library store of patient imaging data must be fused with the surgeon's visual perspective of the surgical field so that a virtual fusion image is presented in correct anatomical alignment and registration. By so doing, the improved imaging modality can have relevance to and can be validated by the surgeon's inherent sense of spatial location, anatomy and general surgical know-to-do derived from years of visual, tactile and kinesthetic sensory experience. The imaging modality thereby would also avoid a need for cumbersome patient registration frames and remote display systems.

Also desirable is a system enabled to segregate elements of the visual field. In a first embodiment, segregation is done to identify individual bones in a dataset derived from tomography or from an AP and Lateral view by X-ray. The individual bones or clusters of bones may then be projected into a synthetic virtual view according to their surgical relevance. It then becomes possible to isolate the bones from the patient and to do more detailed analysis of structure of individual bones and functional interactions between small sets of bones. Segmentation also includes computer power to isolate visual elements such as the hands and fingers of the surgeon, surgical tools and prosthetics while reducing virtual clutter. Surprisingly, when this is done, any relevant virtual elements of the patient's anatomy and a virtual database segmenting the surgeon's hands may be operated cooperatively to show the hands occluding the virtual anatomy—or a virtual pair of hands operating in an enhanced virtual space. These and other inventive systems have not been realized in the art and are an object of the invention and is difficult or impossible to achieve using light-based image analysis and optical fiducials at any wavelength.

Thus, there is a need in the art for an intraoperative three-dimensional virtual viewing system that overcomes the above challenges, is perceptually integrated into the surgeon's view of the operation in progress, includes both haptic and pre-haptic interfaces, and overcomes system blindness when line-of-sight is blocked. Depth-enhanced virtual views of any surgical instruments and prosthetics manipulated by the surgeon are also desirable for making measurements of angles and guidepaths on instrumental approach to a surgical target, such as in implantation of surgical fixators or replacement joints, for example. A novel approach to these and other issues facing modern surgery is described that surprisingly is computationally simple and fast and has been enhanced to rely on the surgeon's touch and gestures as well as virtual image display, thus providing essentially a multi-sensorial extension of the surgeon's senses in integrated computer-assisted surgical navigation systems and methods.

SUMMARY

In at least one embodiment, a method of surgical navigation may include receiving an external three-dimensional model of a surgical site from the viewpoint of a headset, wherein the external three-dimensional model is derived from reflected light. The method may further include aligning the external three-dimensional model with an internal three-dimensional model of the surgical site from the viewpoint of the headset, wherein the internal three-dimensional model is derived from medical imaging, and generating an aligned view. The method may further include providing the aligned view to the headset, and updating the aligned view in real-time while the headset is moved or the surgical site is moved or modified during a surgical procedure.

Surgical medicine can benefit from whole a new generation of information technology advances, particularly in virtual imaging. The embodiments disclosed here are driven by an ever-increasing demand to reduce patient costs and risks, improve patient safety, efficiency, and surgical outcomes. However, development of realistic virtual surgery systems for invasive surgical procedures remains one of the most challenging problems in the field of virtual reality based surgery (and surgical training) because of the complexity of anatomical structures, their changes in pathological states, and the need for detailed information about surgical tools and prosthetics used intraoperatively. While not generally cited, the surgeon's hands should also be considered in any comprehensive answer to the problem, both because they are frequently an obstruction to visual interrogation of the surgical field and because their motion and any gestures made offers information that can inform the system display. When used in combination with a segmented library of anatomical parts, tools and prosthetics, the capacity to also segment the surgeon's hands offers multiple advantages in reducing image clutter, improving depth cues, and directing computing operations without interference from background noise and without the need for remote control interfaces.

While not generally appreciated, the surgeon has the capacity to integrate augmented imagery presented to a single eye with a native visual field presented to an unaided eye. Integration involves the corpus callosum and optic chiasma in the brain, which are neurologically integrated with motor functions in both hemispheres. Thus, embodiments may be designed to take better advantage of this inherent 'wetware' by better aligning the surgeon's pupillary view in the unaided eye with the augmented virtual elements presented through a monocular or headset. A faster image refresh rate and attention to vanishing point geometry in raytrace software, along with high fidelity optical pathways, may be used to achieve the coordination whereby effortless inter-hemispheric coordination of hand-eye motion is realized.

In an embodiment, the surgeon may be wearing a headset having an eyepiece, a camera for collecting reflected light, a projector for projecting an array of light beams onto a surgical field, and an eyepiece projector or optronics element for providing the virtual image onto or through the eyepiece and into the pupil, wherein the headset includes a digital connection to a computing machine having at least one processor, at least one memory for storing the computerized tomographical scan, and programming instructions for constructing the external three-dimensional model from optical data received by the camera and for constructing the virtual image derived from the computerized tomographical scan (or other imaging modality) according to anatomical points of reference detected in the external three-dimensional model. The computing machine may also include a co-processor or a server for generating and analyzing internal and external three-dimensional wireframe models.

The external three-dimensional model may be aligned with a plurality of anatomically correlated emission sources, such as an active radiobeacon, a reflective RFID tag, any radio reflector, or an optical beacon that are enabled to continue to provide orientation information even if the surgical site is blocked by an arm, a surgical instrument, or a machine such as a C-arm.

Surgical instruments may also be tracked, each instrument being modified to emit a signal indicative of a location relative to the external plane of the surgical field. The surgical instrument and eyepiece may be operated cooperatively to display and/or stream numerical data such as depth, angle, relative angle, relative elevation, volume, temperature, pressure, or a more specialized sensor output, such as oxygenation or enervation.

In another embodiment, an umbilical connection to a computing machine and a dot matrix projector is provided so as to relieve the surgeon from a larger headpiece weight. The digital connection may comprise a bundle of optical fibers, and the computing machine may be a server digitally connected to the headset by the optical fibers.

In another embodiment, the surgeon may be enabled to select a part of the virtual image by pointing at the part with a laser pointer, and raise the part away from the surgical field for closer inspection. The part may be manipulated by rotation and magnification according to hand gestures as a virtual image projected into the eyepiece. Software may be used to provide a reference library model from which views of a patient volume can be obtained from any depth and any angle. Individual bones or anatomical elements may be selected for inspection in the virtual field above the surgical site or in situ, including temporal sequences showing a series of surgical events from a surgical plan.

This embodiment may use software to construct 3D models from tomographic datasets and to segment out individual anatomical elements such as bones, and optionally soft tissue features such as organs, nerve tracts and ligaments. Segmentation can be computationally intense and may be done offline before starting the surgical procedure. Segmentation may be performed by a process of comparing datasets with reference datasets on human anatomy and may be confirmed by teaching. Prior to operating, a surgeon may indicate the relative anatomy and may educate the system by pointing to each anatomic element in turn and naming it.

Suitable libraries of segmented images of the patient's anatomy may be stored in computer memory for use during a surgical procedure. The internal images may be acquired by computerized tomography (CT), MRI, or other imaging modalities, for example, while not limited thereto.

Radio signals may be used to supplement the digital mapping and for updating relative alignment and orientation so as to speed the initial fusion and any update required when there has been a break in the visual map continuity. Map elements may be lost when optical data streaming is interrupted, such as by turning the headset away from the surgical field, or by putting a hand on an incision site, and so forth.

Processing the digital data may include performing triangulation based on the one or more acquired signals and a distance relationship between a transmitter that outputs the one or more emitted signals and a receiver that receives the one or more reflected signals. The system may be optically frameless and patient registration may be achieved by an internal to external mapping correlation routine that is directed by the surgeon so that the external wireframe is fused to the solid model of the underlying anatomy. Subsequent updates may be tracked by monitoring the position of the headset, either inertially or with reference to radiobeacons. Individual beacons may be passive reflectors and may be configured to reflect a signal that has an identifiable signature so as to speed acquisition of the general orientation and alignment of the coordinate systems. The radio system may supplement the optic system and allow all the data sets to be brought into a common frame of reference. Advantageously, radiobeacons may be placed at the corners of a Mayo table, a slip-on cover on the Mayo table, the corners of the operating table, or a mat under the surgeon's feet, each corner having a radio reflective antenna equipped with an identifiable signature reflection. In this way, the headset orientation may be tracked by an external reference frame, but one that is not subject to the weaknesses of optical tracking. The surgeon may calibrate the system by pointing out at least one beacon associated with a boney prominence or obvious anatomical feature that is present on the wireframe map and the internal solid model and the rest of the beacons can then be formed into a spatial map that is determinate for the duration of the procedure. If the patient is rolled over, for example, only one or two beacons are disturbed, so their positions may be refreshed while the remaining beacons may be fixed. Tracking the headset may use standard matrix trigonometry and require substantially less computational power.

Alternatively, active radiobeacons may be used, each emitting an encoded identifier. Time of flight (TOF) measurements may be utilized as described here to map each beacon relative to a stable external reference frame achieved by tracking radiobeacons embedded in a surgical drape over the surgical site or positioned on a Mayo table or at the corners of an operating gurney. By determining the distance to an active radiobeacon from several radio receivers, the location of the beacon relative to the reference frame may be accurately determined. These principles can be realized using active or passive radiobeacons.

In another embodiment, a separate optical system may be used to track the pupil and lens curvature of the unaided eye, and an algorithm may be employed to derive a vanishing point that correctly renders the virtual information presented to the augmented eye. In this way, the brain is offered information having sufficient visual depth clues that motor coordination may be informed by the augmented virtual information. For example, the surgeon may not have to look up to read graphical information presented in the augmentation. Data streams may appear to float near to, but not impede, the unaided eye's point of focus.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

FIG. 6 shows an example process flow for generating a three-dimensional virtual fusion view by which at least aspects of surgical navigation may be implemented;

FIG. 7 shows an example process flow for updating a virtual fusion view by which at least aspects of surgical navigation may be implemented;

FIG. 12 shows an example dot array by which at least aspects of surgical navigation may be implemented;

FIGS. 16A and 16B show an example process flow for building a three-dimensional virtual fusion view by which at least aspects of surgical navigation may be implemented;

FIG. 19 shows an example headset view of a levitate command by which at least aspects of surgical navigation may be implemented;

DETAILED DESCRIPTION

Figure 1:
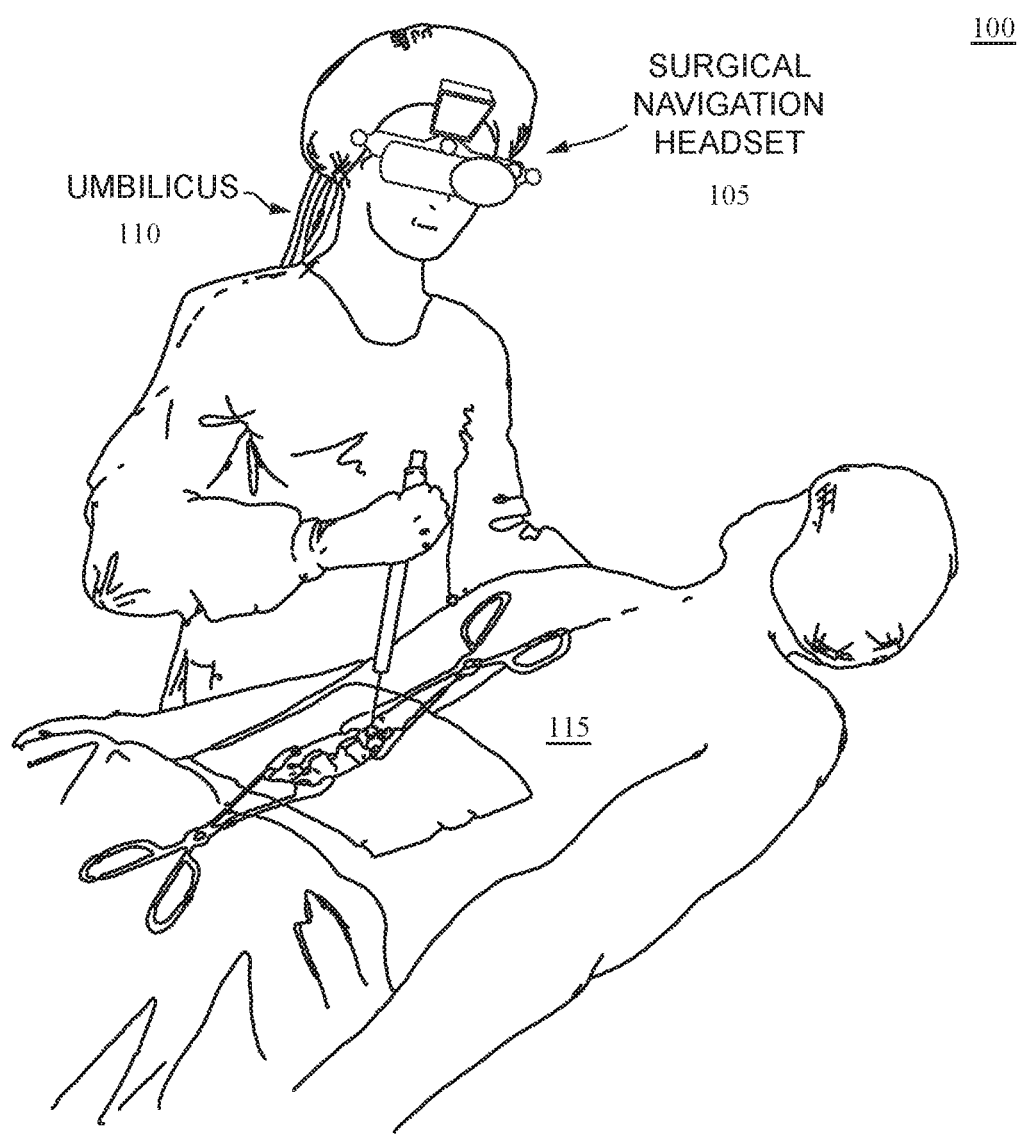
FIG. 1 shows an example system by which at least aspects of surgical navigation may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Certain terms are used throughout the following detailed description to refer to particular features, steps or components, and are used as terms of description and not of limitation. As one skilled in the art will appreciate, different persons may refer to the same feature, step or component by different names. Components, steps or features that differ in name but not in structure, function or action are considered equivalent and not distinguishable, and may be substituted herein without departure from the present disclosure. Certain meanings are defined here as intended by the inventors, i.e., they are intrinsic meanings. Unless otherwise defined, all technical and scientific terms used herein have the same meaning as commonly understood by one of ordinary skill in the art to which this disclosure belongs. In case of conflict, the present specification, including definitions, will control. The following definitions supplement those set forth elsewhere in this specification.

"Computer" refers to a virtual or physical computing machine that accepts information in digital or similar form and manipulates it for a specific result based on a sequence of instructions. "Computing machine" is used in a broad sense, and may include logic circuitry having a processor, programmable memory or firmware, random access memory, and generally one or more ports to I/O devices such as a graphical user interface, a pointer, a keypad, a sensor, imaging circuitry, a radio or wired communications link, and so forth. One or more processors may be integrated into the display, sensor and communications modules of an apparatus of the invention, and may communicate with other microprocessors or with a network via wireless or wired connections known to those skilled in the art. Processors are generally supported by static (programmable) and dynamic memory, a timing clock or clocks, and digital input and outputs as well as one or more communications protocols. Computers are frequently formed into networks, and networks of computers, including servers, may be referred to here by the term "computing machine." In one instance, informal internet networks known in the art as "cloud computing" may be functionally equivalent computing machines, for example.

"Server" refers to a software engine or a computing machine on which that software engine runs, and provides a service or services to a client software program running on the same computer or on other computers distributed over a network. A client software program typically provides a user interface and performs some or all of the processing on data or files received from the server, but the server typically maintains the data and files and processes the data requests. A "client-server model" divides processing between clients and servers, and refers to an architecture of the system that can be co-localized on a single computing machine or can be distributed throughout a network or a cloud.

"Processor" refers to a digital device that accepts information in digital form and manipulates it for a specific result based on a sequence of programmed instructions. Processors are used as parts of digital circuits generally including a clock, random access memory and non-volatile memory (containing programming instructions), and may interface with other digital devices or with analog devices through I/O ports, for example.

"Software" may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is considered limiting.

"Data fusion" refers to the process of integration of multiple data and knowledge representing the same real-world object into a consistent, accurate, and useful representation.

"Segmentation" relates to image analysis in which individual structural elements in a three-dimensional image are abstracted from the image and individually modeled. Once modeled, those elements may be manipulated independently.

"Jitter" refers to the level of variation in a clock frequency per cycle.

"Sampling rate" refers to the number of measurements made per interval of time.

"Synchronous upsampling" as applied here relates to extrapolating a smooth measurement from a stepwise digital measurement by continuously evaluating a bracket of measurements with a slight lag from a real-time data acquisition rate.

"Bit depth" indicates the level of resolution in a binary digital measurement scale.

"Arthrospatial" relates to the spatial disposition of anatomical features in a solid model, particularly applying to boney structures.

"Polar Coordinate system" refers to a spatial mapping system having a fixed Centerpoint point (analogous to the origin of a Cartesian system) called the "pole", where the ray from the pole in the fixed direction is the polar axis. The distance from the pole is called the radial coordinate or radius, and the angle is the angular coordinate, polar angle, or azimuth. In three-dimensions, a "z" depth is also used to define the position of a point in an array relative to the pole.

"Surgical navigation" as used here relates to a method for conducting a surgical procedure using augmented views of the surgical field, of tools, of prosthetics, or of the surgeon's hands, including a virtual model of patient anatomy, preferably with segmentation of individual anatomical elements. The position of the tip of an instrument, for example, may be conveyed to the surgeon by an imaging system (i.e., a system that relies on transmission or reflection of an applied energy to calculate the position of the tip relative to the anatomy). Machine feedback may also be incorporated and used as a complement to human senses of sight and touch as used to guide surgery.

"User interface" refers to a feature of a computing system configured to convert a user signal such as a selection or a gesture into a machine command or a response to a machine request for input.

"Haptic" refers to the quality of a user interface enabled both to display images and to respond to touch commands applied to the interface. Haptic commands can be applied to the surface using a finger on a capacitive, inductive, pressure or temperature-sensitive panel or screen. The term "tactile" refers to the sense of touch, while the broader "haptic"

encompasses both touch and kinesthetic information, or a sense of position, direction, motion and force.

"Pre-haptic" is used to denote a user interface in which gestures in free space are used to command execution of computer-driven routines. Gesture control may include a joystick on a gaming console, a button on a machine, a virtual "soft" button on a capacitive or inductive panel or screen, a laser pointer, a remote pointer, a mouse or keyboard for controlling with cursor, and also verbal commands, while not limited thereto. Pre-haptic commands can also include arm or finger motions as a vocabulary of gestures recognized by an interface camera or an inertial sensor, for example. A combination of a pre-haptic and a haptic interface is also conceived here.

"Stereopsis" refers to the perception of depth and three-dimensional structure obtained on the basis of visual information deriving from two eyes by individuals with normally developed binocular vision. Illusions of stereopsis may be simulated using raytrace software for creating a two-dimensional perspective view in a monocular such that the perspective is a convincing representation of a scene having the needed vanishing points and other visual clues consistent with a depth of field having good correspondence between the visual perception and motor feedback obtained by reaching into the visual field.

"Palmar" is used to describe the densely enervated anterior side of the hand, including the palm, fingers and fingertips, while "dorsal" is used to describe the back of the hand. The hand generally begins at the distal end of the wrist joint defined by the radius and ulna. The palmar aspect of the hand includes the dermis, an underlying palmar aponeurosis attached to the dermis by minute fasciculi, and underlying nerve roots and tendons.

General connection terms including, but not limited to, "connected," "attached," "conjoined," "secured," and "affixed" are not meant to be limiting, such that structures so "associated" may have more than one way of being associated. "Fluidly connected" indicates a connection for conveying a fluid therethrough.

Relative terms should be construed as such. For example, the term "front" is meant to be relative to the term "back," the term "upper" is meant to be relative to the term "lower," the term "vertical" is meant to be relative to the term "horizontal," the term "top" is meant to be relative to the term "bottom," and the term "inside" is meant to be relative to the term "outside," and so forth. Unless specifically stated otherwise, the terms "first," "second," "third," and "fourth" are meant solely for purposes of designation and not for order or for limitation. Reference to "one embodiment," "an embodiment," or an "aspect," means that a particular feature, structure, step, combination or characteristic described in connection with the embodiment or aspect is included in at least one realization of the present disclosure. Thus, the appearances of the phrases "in one embodiment" or "in an embodiment" in various places throughout this specification are not necessarily all referring to the same embodiment and may apply to multiple embodiments. Furthermore, particular features, structures, or characteristics of the present disclosure may be combined in any suitable manner in one or more embodiments.

Referring to the figures, FIG. 1 shows an example system 100 by which at least aspects of surgical navigation may be implemented, arranged in accordance with at least some embodiments described herein. A headset 105 worn by a surgeon may include a projection system for displaying a virtual view of a solid model of internal bones and organs in an eyepiece. The projection system may be driven by a computing environment that may be local or remote, for example including an umbilicus 110 to transmit data from a remote computing machine with processor, memory and program-specific instructions. Alternatively, computing hardware may be belt mounted or even miniaturized for mounting as part of the headset 105. In a preferred embodiment, data exchange may be conducted to and from the headset 105 through a databus optionally including fiber optics in the umbilicus 110. The headset 105 may also include a light pattern projector for casting an array of dots, either as a random speckled pattern or as a structured array, onto the surgical field 115. This pattern is then captured by a pair of cameras with frame grabbers mounted so that different angular views taken at a single instant may be used to triangulate the position and elevation of unique dots identifiable in both captive images. Reflected light specific bandpass filters may be used to reduce false signals from ambient light; further specificity may be obtained in brightly lighted environments by strobing the excitatory projector.

Once a wireframe map of the surgical field 115 is obtained, anatomical reference points may be identified by image analysis or may be assigned by an operator, and a solid model may be oriented and aligned so that the anatomical features not visible beneath the exterior view of the surgical field 115 may be matched and projected in the virtual view displayed in the eyepiece. The solid model data may be acquired from computerized tomography (CT) scans, magnetic resonance imaging (MRI), or other scans already of record in the patient's digital chart. In a general computational approach, thin slices may be merged to generate a solid model, and the model may be digitally segmented to isolate individual anatomical structures such as bones, vessels, organs and the like.

The computing environment provides the resources to do a data fusion of the two image datasets (the external view and the solid model) and to continuously update this according to the viewpoint of the eyepiece, which may be updated by inertial guidance or in reference to beacons placed around the margins of the field of view, for example, so that a simple reverse triangulation provides the spatial location and elevation of the eyepiece from the reference beacons. These beacons may be optical or radiobeacons, for example, the radiobeacons enabling updated tracking of the solid model even when a visual obstruction or lack of light blocks the camera view. Advantageously, the system can thus continue to operate for short periods even in complete blackness, such as in the event of a power failure, if provided with backup power.

Figure 2:
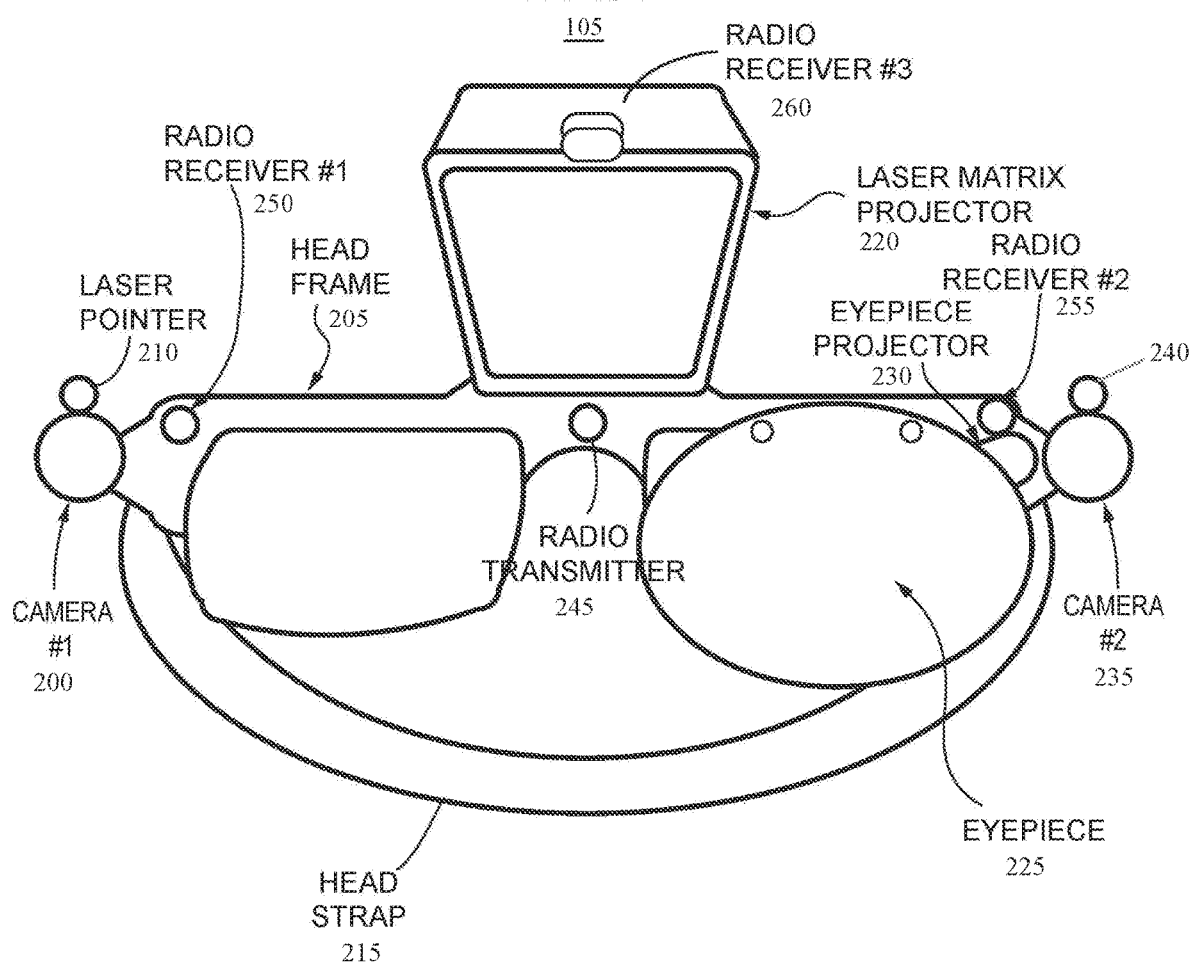
FIG. 2 shows a frontal view of an example headset by which at least aspects of surgical navigation may be implemented.

FIG. 2 shows a schematic frontal view of the headset 105 of example system 100 of FIG. 1, arranged in accordance with at least some embodiments described herein. Shown from left to right are: a pod-mounted camera 200 on a headframe 205 that is worn over the eyes. Above the camera 200 is a small diode laser pointer 210 that is keyed to identify where the camera 200 is pointed and may be used for adjustment. The head frame 205 may include a nose bridge and right and left lens supporting arms. A head strap 215 may be used to secure the headset 105 in place. Center top is an infra-red dot projector 220 serving to paint the surgical field with a fine pattern of dots. As shown here, a single eyepiece 225 is worn. The eyepiece 225 operates with an eyepiece projector 230 to display a virtual solid model view of the surgical field to the eye of the wearer. Alternatively, the eyepiece 225 may extend across both eyes of the user. A second camera 235 with a laser pointer 240 is mounted on the opposite side of the head frame 205. Both cameras may be slaved to frame grabbers either by CCD or CMOS chips that are synchronized to capture an image of the dot pattern at a precise instant of time. The cameras may be slaved to a master clock so that dot pulse rate is coincident with image capture or the projector 220 may be operated continuously and both cameras operated with an adjustable but simultaneous frame capture rate. Raytrace software may be used to impart a generally stereoscopic view of the surgical field and underlying structures. The intent is to provide the user with an image that appears to be a three-dimensional representation of the underlying anatomy, such that it validates the surgeon's inherent sense of spatial location, anatomy and surgical know-to-do derived from visual, tactile and kinesthetic senses. All visual features may be presented as superimposed on the patient body form in correct anatomical alignment and registration.

Methods for projecting a realistic virtual view continue to improve. Recent art includes US Pat. Publ. No. 2015/016777 to Magic Leap, which describes planar waveguides, piezo drive units, vibrating optical fibers, Bragg gratings, and other improvements of optoelectric eyewear that enable the presentation of a virtual image to a viewer as if projected in real space and can include eye tracking. Also of relevance are U.S. patent Ser. Nos. 13/915,530 and 14/205,126, all of which are hereby incorporated by reference.

A radio emitter 245 is shown centerwise at the brow of the headset and may be used in conjunction with radiobeacons, RFID chips or other radio reflectors as described in more detail below to aid and guide in registration of the virtual image with the eyepiece display 225. Radio receivers 250, 255, 260 having defined spatial geometry may be mounted on the outside ends of the headset 105. Using laser beams, LIDAR may also be used to construct a radiometric landscape of the surgical field. The imaging system thereby overcomes the need for cumbersome patient registration frames, reflective fiducials, and remote display systems.

Figure 3:
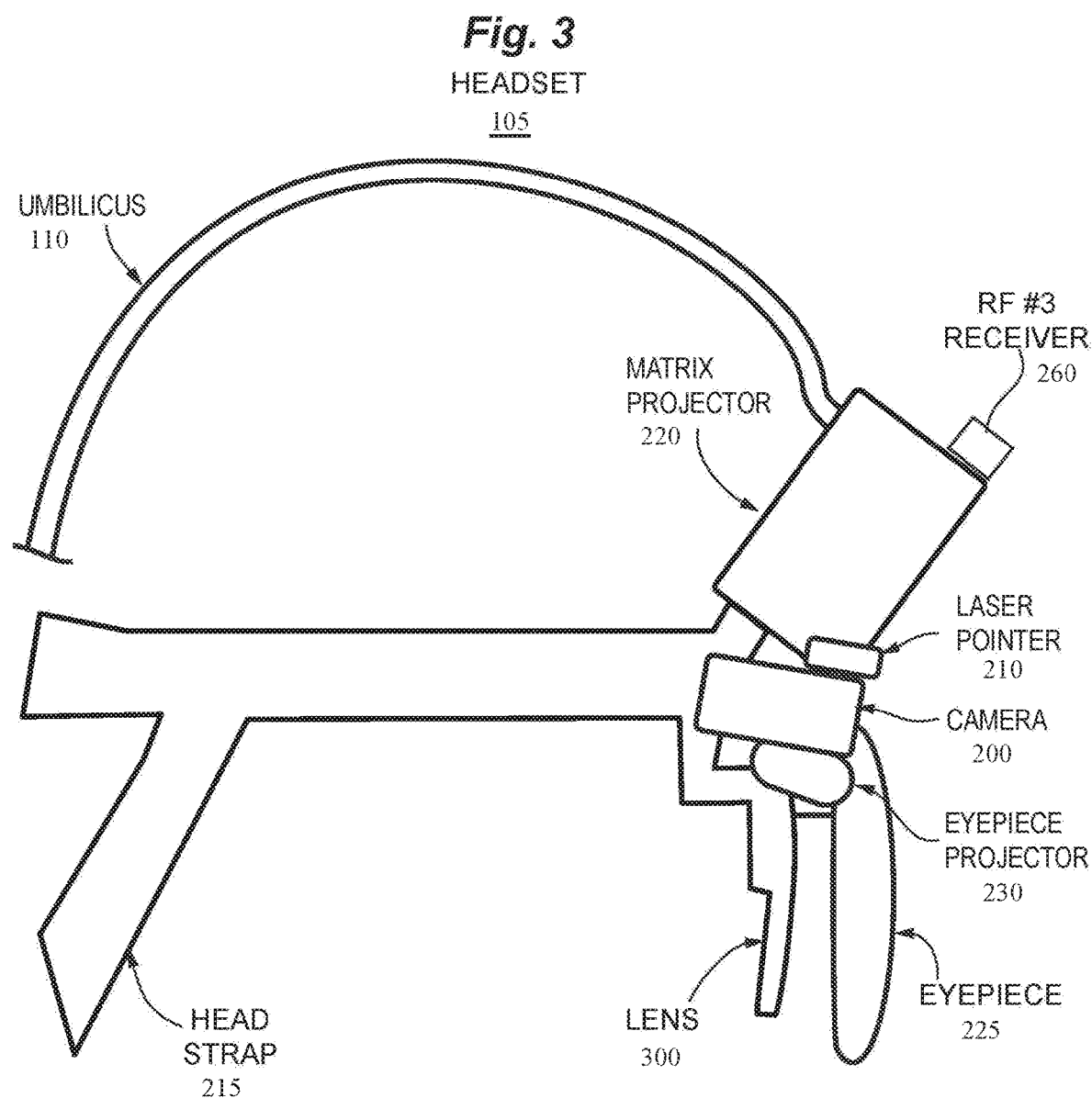
FIG. 3 shows a side view of an example headset by which at least aspects of surgical navigation may be implemented.

FIG. 3 shows a schematic side view of the headset 105 of example system 100 of FIG. 1, arranged in accordance with at least some embodiments described herein. In this view, the headset 105 is supplied with lenses 300 that may work cooperatively with the eyepiece 225 to aid in displaying three-dimensional "see into" images to the retina of one eye or both eyes.

Also shown here is the umbilicus 110 for data transfer to and from the headset 105 to a remote computing environment. Computational tasks may be divided between local functions of a headset microcomputer and controller, and a workstation or networked processing environment operating over distributed workstations, either inside or outside the operating suite.

Large amounts of data may be needed in addition to any camera images captured by the headset 105. A CT solid model typically consists of millimeter-thick sections that have been fused using a pixel-based extrapolation process into a solid model.

Surgical navigation of the present disclosure relies on an accurate three-dimensional solid model of the patient. Data libraries having this data may be acquired through a number of medical imaging technologies including CT, MRI, x-rays, quantitative ultrasound scans, and so forth. Scans using a variety of methods, such as CT and MM can sometimes be combined with other datasets through data fusion techniques. The objective is the creation of a three-dimensional solid model that accurately depicts the anatomical volume under the surgical field. Of the available scanning methods, a primary CT model is preferred because MM data sets may have volumetric deformations that may lead to inaccuracies. For example, a data set may include the collection of data compiled with 200 CT slices that are 1 mm apart, each having megapixel density. Pixel contrast provides sufficient detail of soft versus hard tissue structures to allow a computer to differentiate and visually separate the different tissues and structures. The model may then be registered with anatomical landmarks in the surgical field so that any projected virtual image in the eyepiece 225 is correctly registered with respect to the relative positions of the patient and the surgeon, and is then updated in real-time to maintain this correctness. Large memory resources and algorithms for image correlation may be used to make fine adjustments in the display presented to the surgeon.

Where needed, the solid model may be supplemented by reference anatomy models, such as for reconstructive surgery and for supplementing CT scans with standard soft tissue landmarks.

In a preferred embodiment, the surgeon may light up the reference landmarks using a laser beam, pointing at significant reference features and stating an anatomical name that is recognized by the system, so that the surgeon essentially teaches the system the mapping points to be used in stabilizing the images so as to smooth real-time scanning as the headset 105 is moved, and so as to prevent loss of coherence when objects such as the surgeon's hands obstruct the solid model view and the external view.

The resulting virtual model constructs and integrates patient-specific, anatomically correct, and comprehensive three-dimensional models, with any soft and hard tissue details available. Advantageously, having this information allows the surgeon to highlight a particular feature, such as an L3 lumbar vertebra, and abstract it above the surgical field for closer inspection. The solid model of the vertebra may be rotated and sectioned, angles may be measured, and the vertebra reinserted into the spine of the patient in a virtual space, complete with an intended track to be followed by a drill, and information sufficient to identify the size of screw that is optimal, for example. Calling out the L3 or T12 vertebra may be done with a laser pointer, a pointing finger, or a verbal command, for example.

Data concerning dimensions and angles may be displayed on the eyepiece 225 and verbal commands may be used in conjunction with a laser pointer to project lines through the body and measure cross-sectional areas, for example. Measurement data are generally transmitted to a remote computing environment, and display views may be transmitted back to the headset 105. Several devices for projecting a virtual view onto an eyepiece are known in the art.

Figure 4:
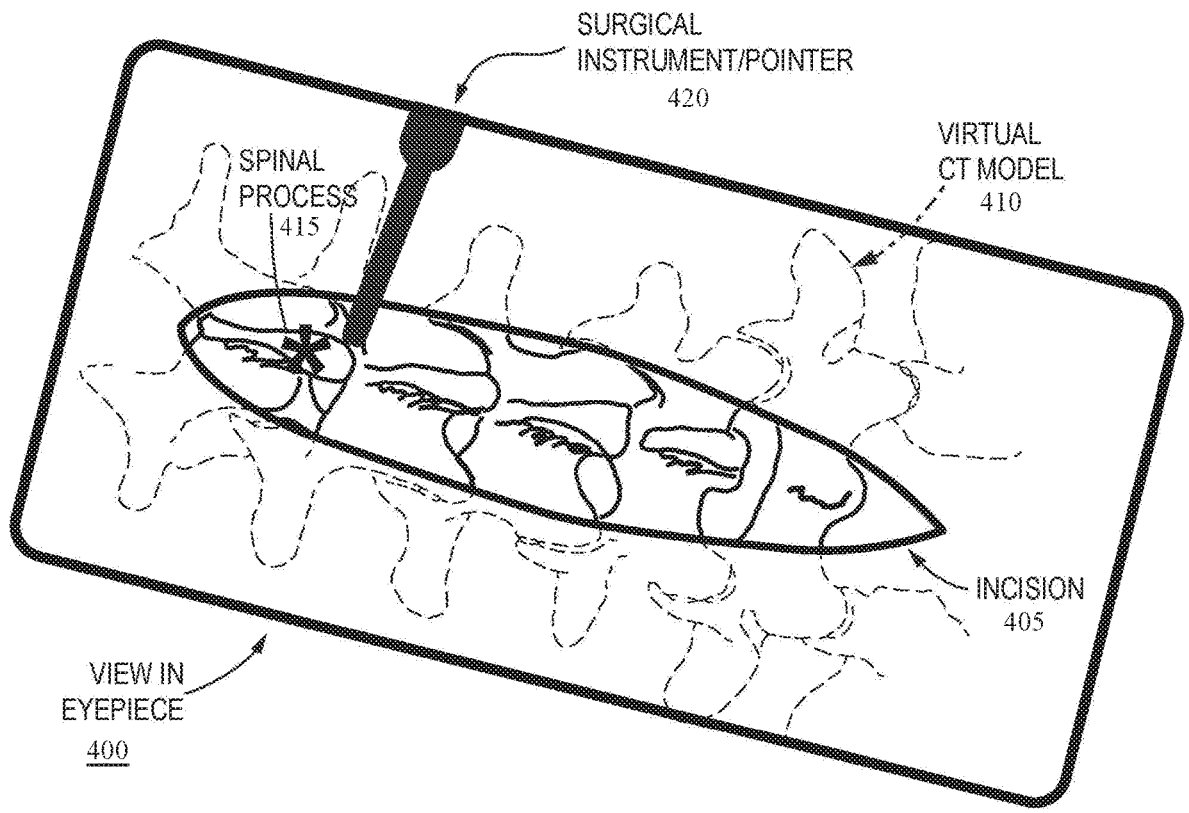
FIG. 4 shows an example headset view of a surgical field by which at least aspects of surgical navigation may be implemented.

FIG. 4 shows an example headset view 400 of a surgical field by which at least aspects of surgical navigation may be implemented, arranged in accordance with at least some embodiments described herein. The headset view 400 shows an incision 405 and a virtual CT model 410 of underlying boney structures in anatomical registration.

Shown in this example is T12, the last thoracic vertebra, and a section of exposed lumbar vertebra as would be operatively exposed to repair a fractured pedicle or facet joint. Each vertebra may be identified by a spinous process 415 that is visible through surrounding fascia. If needed, a tool with a radiobeacon or light emitting diode may be used to identify the exposed anatomical features in the surgical view 400 as a first step in aligning a CT model with the patient as supine on an operating table. With increased sophistication, image analysis may be used to identify the relevant anatomical landmarks automatically.

Shown are the lumbar vertebrae and a partial view of the sacrum adjoining the iliac crest. Radiobeacons may be placed as markers to accelerate re-alignment of the display when the surgeon blocks the visual view with an arm or looks away.

Surgical instruments 420 may also be tracked, such as for apparent depth of penetration. Each instrument is generally logged into a library of instruments stored in a computer memory, and position, alignment and registration may be done continuously during the procedure so that no tools are left behind.

Figure 5A:
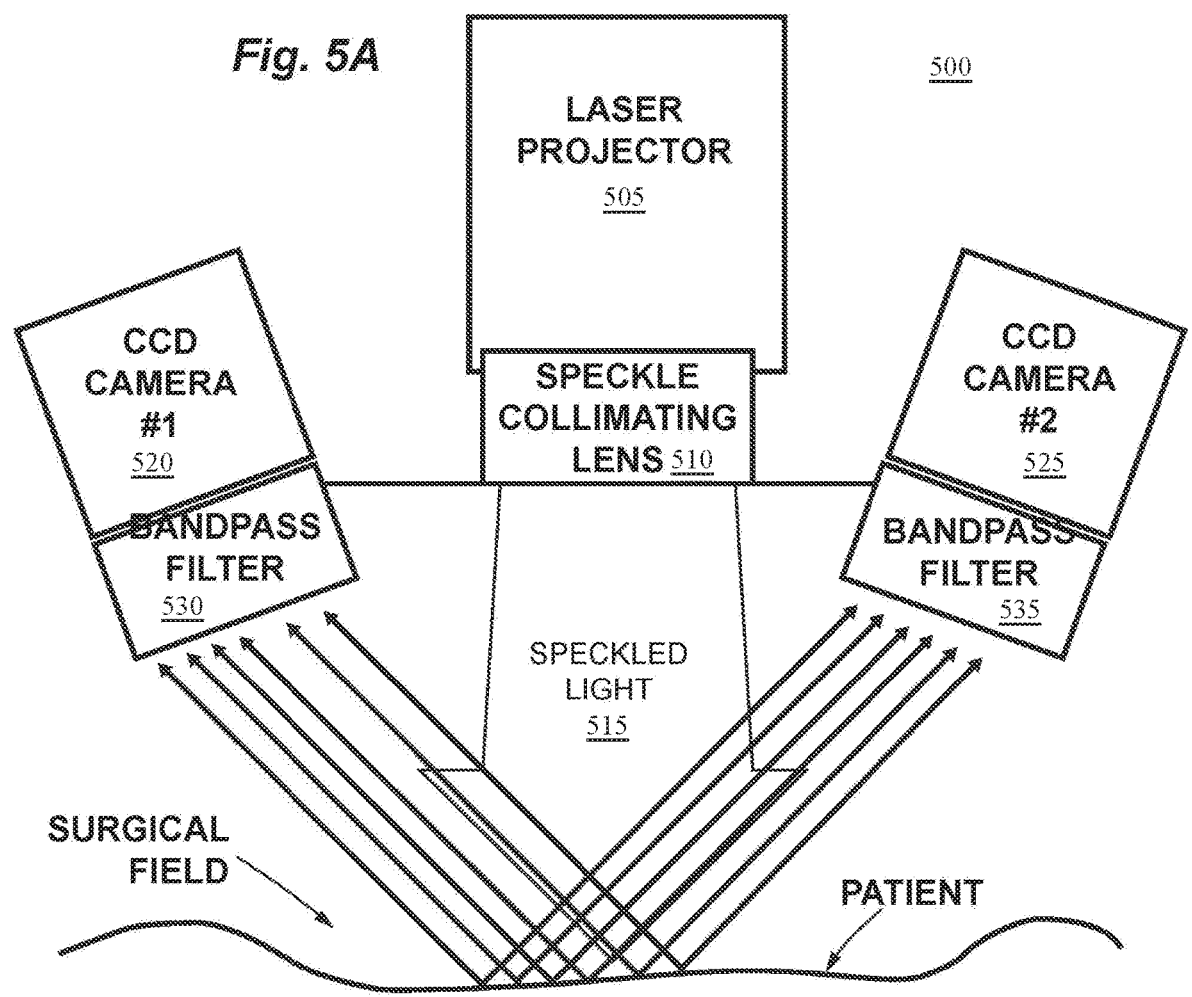
FIG. 5A shows an example mapping system for generating a three-dimensional external model of a surgical field by which at least aspects of surgical navigation may be implemented.
Figure 5B:
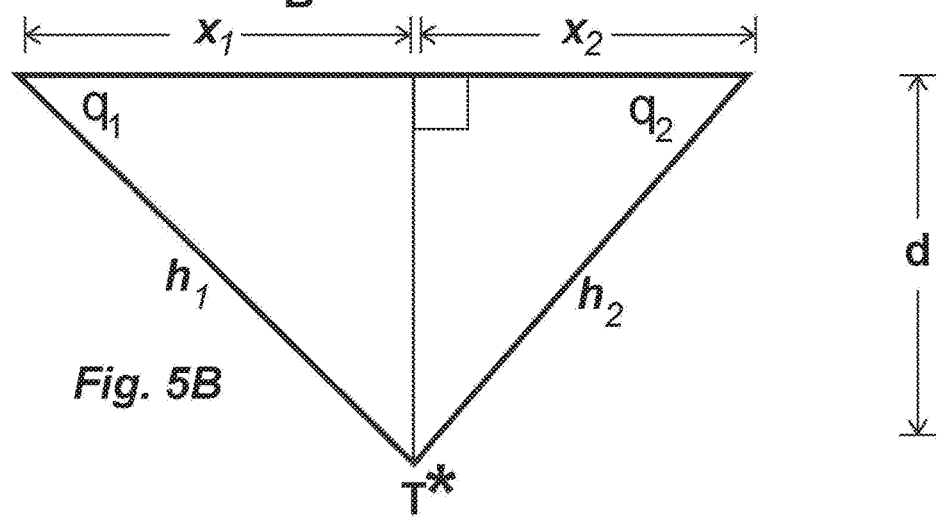
FIG. 5B shows an example data transformation by triangulation to generate an array of Cartesian datapoints.

FIG. 5A shows an example mapping system 500 for generating a three-dimensional external model of a surgical field by which at least aspects of surgical navigation may be implemented, arranged in accordance with at least some embodiments described herein. In this example, a depth map may be constructed from a generally random pattern of speckled light 515 painted onto the surgical field by a projector 505. A collimating lens 510 may be used to extend the coherency of the spots to a useful distance. A detailed three-dimensional external wireframe model of the surgical field may then be constructed from images captured by two cameras 520 and 525 at a single instant but from different angles. FIG. 5B shows an example data transformation by triangulation to generate an array of Cartesian datapoints having depth and position.

The apparatus of FIG. 5A utilizes an illuminated-pattern projector 505 for painting the surgical field and a pair of cameras 520 and 525 for capturing the dot pattern as projected. As can be readily appreciated, the projector 505 may include one or more light emitting diodes (LEDs), or a higher powered laser with a beam splitter, which may transmit the light through a lens and/or other optical train to produce a desired dot pattern output. The size of the dot array is scaleable, and the level of detail achieved is dependent on the collimating lens 510 used to project coherent light onto the subject. With proper attention to detail, submillimeter resolution is possible. As the surgeon moves closer to the subject, the dot pattern projected from a head-mounted system becomes more dense, so that resolution is a function of distance.

The cameras 520 and 525 may each include a CMOS (Complementary Metal-Oxide Semiconductor) or CCD (charge-coupled device) sensor for collecting a pixelated image of the surgical field. Note that in FIGS. 1 and 2, the dot matrix projector and cameras are shown as visible from the front view, although they may actually only be visible through an intervening component such as a lens and/or filter.

For example, bandpass filters 530 and 535 may be used to filter out undesirable signals such as from ambient light or body heat. For noise reduction, a relatively narrow slice of the far infrared wavelengths (e.g., 1050-1150 nanometers) may be used, as may be generated from a miniature YAG laser. One way to make the images generally robust against sources of interference such as sunlight is to use the bandpass filters 530 and 535 in conjunction with digital rolling shutters that are synchronized with strobing of the LED projector 505. Strobing in general allows higher processing speed, as well as reduced energy consumption and limits the need for cooling of the electronics.

In general, the IR projector 505 may be a single emitter that transmits an optically-focused pattern including a plurality of spots or "dots" that optically populate the field of view. The projector 505 may transmit IR light via optics, such as through a multi-lens array, a diffraction grating, and/or prismatic or Fresnel-based technology, which creates a pattern of a plurality of well-defined light spots. Alternatively, multiple light sources may be used, and indeed, this allows for different, per-spot parameters such as timing, intensity, and other unique encoding signatures that facilitate individual spot correlation and pattern recognition.

A pair of light-sensitive cameras 520 and 525 placed off-axis from the transmitter acquires any reflected spot pattern from a reflective surface within range. For example, the reflected dot pattern may be gathered by a focusing lens in the receiving element onto the surface of the sensor's imager and captured by a frame grabber so that the two frames (one from each camera) are captured at a single instant of time. Alternatively, a single light-sensitive camera (having appropriate filters) placed off-axis from the transmitter acquires any reflected spot pattern from a reflective surface within range. For example, the reflected dot pattern may be gathered by a focusing lens onto the surface of the sensor's imager and a more computationally intensive process may be used to calculate spot positions and a depth map therefrom.

To this end, because the baseline separation of the two cameras (or between the dot matrix projector and the camera) is known, a triangulation algorithm may be used to determine depth and position. One or more spots in the projected pattern allow for computation of a distance result, e.g., as in the top view of FIG. 5A, where the body surface represents a reflective surface, the solid lines represent the transmitted beams and the dashed lines represent reflections incident on the camera lens. Even more spots in the projected pattern allow the detection of a change in the reflective entity's elevation and/or orientation, as in the simplified two-dimensional view of FIG. 5B where the sensor detects an example target T*. The actual implementation may be more complex because the headset may be tilted on multiple axes.

Where blue, purple, violet or ultraviolet light is used to generate a dot matrix pattern, corresponding camera optics and bandpass filters are needed to acquire images suitable for depth and position mapping.

A processor with sufficient volatile memory and clock speed may run an algorithm or set of algorithms to calculate the geometric offsets of each spot, e.g., based upon its centroid. Along with a distance, a change in floor elevation and/or surface orientation may be computed.

The distance calculation is generally invariant to the spot intensity and is based upon digital data so as to be less susceptible to analog interference. The dot matrix projector 505 may be dynamically adaptive to provide intensity adjustment according to the ambient lighting, surface properties, and the required sensitivity. For example, when dots are output onto a highly reflective surface, less intensity may be output, and conversely more intensity may be output for a surface such as skin that does not reflect particularly well. Any suitable frame rate may be used depending on the application, e.g., 15 to 500 frames per second, or even higher, with a suitable camera selected based upon the needed/desired frame rate. A typical frame rate may be about 50 fps, but the faster the frame rate, the less latency, such as for obstacle detection, and the more data is available for processing (e.g., if needed to discard poor map quality images). The timing may be such that the beam output is pulsed, with background correction being made based on background intensity between pulses. A chopper may also be used.

A signature may be encoded into the dot matrix signal, e.g., via pulsing, to further provide robustness. In this way, for example, a reflected signal received at an allowed frequency and/or at the correct synchronized time, but that does not have the correct signature, may be rejected as likely being from interference.

The detected distance may be used for obstruction detection, for example. The geometry and/or displacement of each spot may be used in the computation. Note that in a situation where no reflection is sensed, beacon inputs may be used to determine whether the system is faulted or the cameras are simply not pointed at the surgical field.

Lasers may include diode pumped YAG lasers that advantageously may be obtained in a range of sizes down to about 1 cm$^3$ and that may have well-defined homogeneous frequency output at about 1080 nanometers. Doubled neodymium YLF/YAG lasers are also preferred for their small size and low cost. Q-switched microlasers are well suited for strobing applications although somewhat larger in size. DFB lasers are tunable, and may be useful in defining spot signatures, and are very small. Alternatively, blue, violet and UV lasers may be used such as described in U.S. Pat. No. 6,002,695. Typically, UVA and UVB emissions associated with tissue damage are avoided, but some violet and long UV wavelengths have been associated with skin wound healing.

Fiber coupling permits larger laser packages to be projected onto the surgical field via an umbilicus as shown in FIGS. 1 and 3. DPY lasers also may be investigated if desired. Thus the laser package is readily obtained from commercial sources and may be provided with a lens system suitable for generating a random dot pattern or a structured light pattern as will be described below.

Blue, violet and UV lasers include Nitrogen lasers, excimer lasers, metal-vapor lasers, but more generally may include purple lasers such as Krypton and Argon excitation, GaN laser, and certain dye lasers. Reflected light and fluorescent emissions may be enhanced with filters.

Alternatively, analyzing the geometric movement of spots, e.g., by processing to find the centroid, provides one means of analyzing spot data to produce a depth map with a single camera, although this demands higher levels of computing power. Having multiple independent spots provides redundancy and robustness of the imaging system. By encoding certain spots, patterns may be more readily recognized, speeding the process of mapping.

FIG. 6 shows an example process flow 600 for generating a three-dimensional virtual fusion view by which at least aspects of surgical navigation may be implemented, arranged in accordance with at least some embodiments described herein. In Step 1 of this embodiment, two cameras are used to draw a correlation map based on images of spots painted on the target by a suitable dot projector system.

In Step 2, the correlation mapping assumes no particular geometry of spots and may be a goodness-of-fit difference map of spot centroids or pairing in the two images. The correlation model may consist of data fields having a position and an elevation and may be used to draw a wireframe model from which anatomical features may be identified.

In Step 3, the wireframe model and a reference 3D solid model (such as from a CT scan) may then be processed by data fusion processing as known in the art to produce a virtual solid model, termed here a "fusion 3D model" extending from the surface of the surgical field to any internal structures observable in the CT scan, as correctly registered according to the body position and observable anatomical features that were captured in the earlier step. If needed, beacons may be used to assist in registration, or an instruction subroutine may be run where a surgeon points out the relevant registration guides on the external wireframe model and in the CT solid model so that the computer may propagate the alignment and generate virtual views of the model for projection into the eyepiece, where the images may be further lensed if needed so as to be correctly portrayed on the retina of the wearer.

The process is iterative. FIG. 7 shows an example process flow 700 for updating a virtual fusion view by which at least aspects of surgical navigation may be implemented, arranged in accordance with at least some embodiments described herein. Several stages of each iteration are identified in FIG. 7. Process flow 700 may include various operations, functions, or actions as illustrated by one or more of blocks 705, 710, 715, 720, 725 and/or 730. Process flow 700 may begin at block 705.

Block 705 may refer to pulsing a dot pattern on the surgical field. Block 710 may refer to identifying and then mapping reflections (any light returning to a camera lens). Block 715 may refer to identifying anatomical landmarks in a wireframe model of the surgical field. Block 720 may refer to fusing the dataset with a three-dimensional solid model. Block 725 may refer to using the resulting "fusion 3D model" to generate virtual images for projection onto the eyepiece of the headset. Block 730 may refer to updating the eyepiece position and angulation. Process flow 700 may be repeated at a speed sufficient to assist the surgeon and validate surgical intuition and direct observation during the surgical procedure. In advanced steps, surgical instrumentation may also be tracked, and geometric calculations needed to orient and properly perform surgical steps may be shown in virtual tracks projected onto the virtual fusion image.

In one instance, a probe may be manipulated to penetrate the body anatomy under the direct observation of the surgeon. The surgeon retains a view of the surgical site and can directly control the implement according to best judgment, using the added three-dimensional view as an aid in successfully completing the procedure with a higher level of accuracy and confidence.

As needed, individual bones or anatomical features may be highlighted and zoomed in for a closer look, or picked up and raised into a virtual space above the surgical field, where they can be studied in rotation or section, picking out cross-sectional areas, lengths, widths, depths, fractures, bone density measurements, and the like so as to validate surgical judgments as to the best approach to the task at hand. Interferences may also be assessed and anatomy may be heuristically compared with reference models to assess reconstruction where, for example, complex fracture and dislocation has occurred. The condition of soft tissue may also be studied by superimposing additional scans such as an MRI in path view. The approach is flexible and scaleable, allowing the surgeon to augment the power of a basic structural fusion view (combining an external wireframe with an internal CT solid model) with an MRI solid model or ultrasound Doppler views, for example.

The position and alignment of the headset cameras or radio receivers may be fixed and known relative to the position and alignment of the headset's emitters. As a result, the change in the geometry information of the illumination spot (or laser highlight) may be algorithmically calculated by comparing frame captures from each of the two sensors (or by comparing time of flight for radio chirps) to produce an accurate distance to a reflective entity (e.g., an object or surface) within the surgical field of view. Use of unstructured and structured light to map surfaces are described in US Pat. Publ. Nos. 2013/0100256 and 2014/0016113. These publications are hereby incorporated by reference.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

Figure 8A:
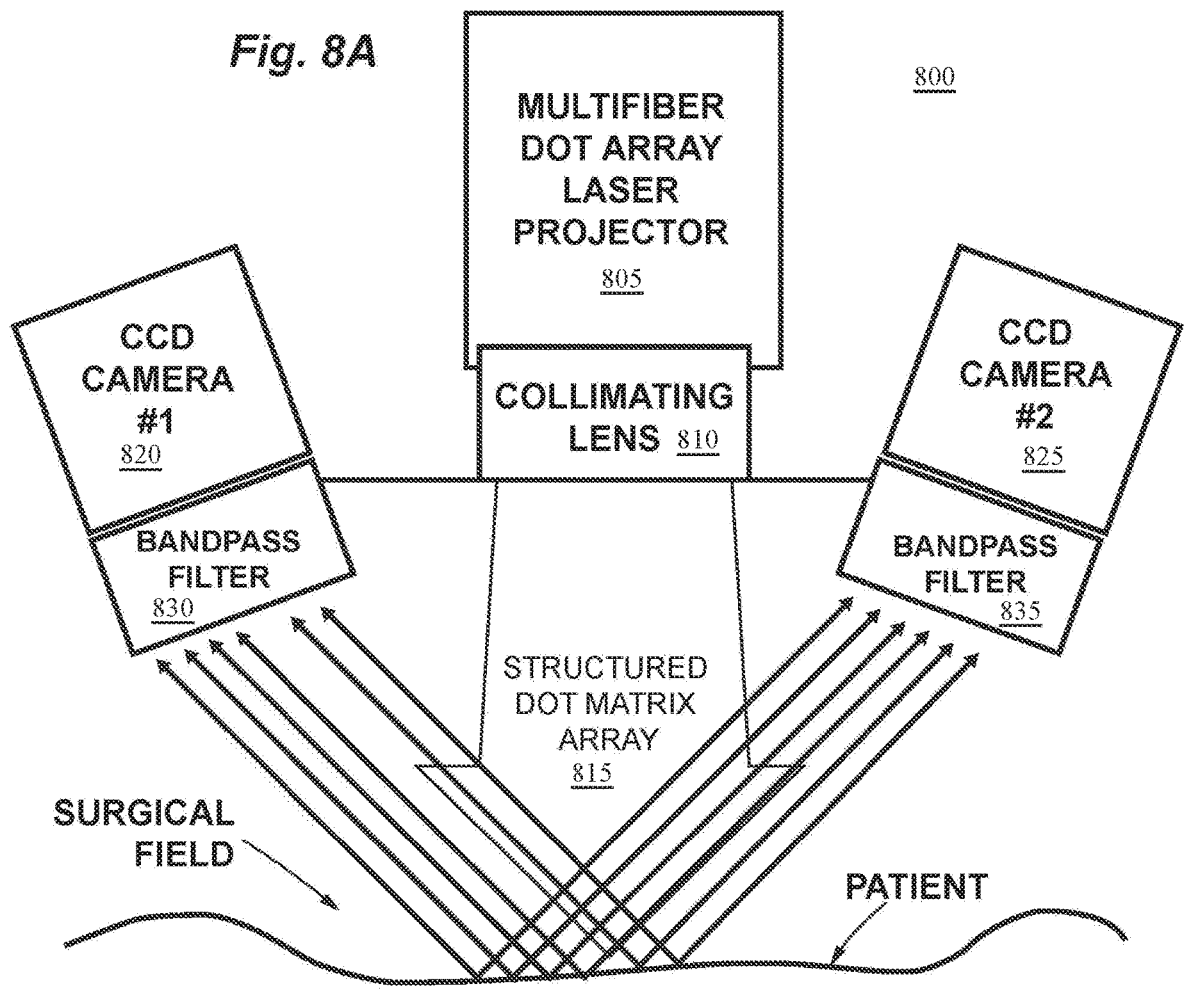
FIG. 8A shows an example mapping system for generating a three-dimensional external model of a surgical field by which at least aspects of surgical navigation may be implemented.

FIG. 8A shows an example mapping system 800 for generating a three-dimensional external model of a surgical field using structured light by which at least aspects of surgical navigation may be implemented, arranged in accordance with at least some embodiments described herein. In this embodiment, an array of fiber optics is used to convey structured arrays of pulsed spots to a collimating lens 810, which projects the light onto the surgical field. Laser diode collimators for laser pattern generators are known in the art. In these views, the dot matrix projector 805 is mounted on the headset 105, however, an overarching C-arm, a chest mount, or a ceiling mount may provide advantages in some operating theaters. An alternate projector may also be available. And by using supplemental beacons, obstructions to the dot pattern may be tolerated by continuing to monitor position at a radio frequency and relying on the computational power of the system to make accurate extrapolations of the underlying anatomy.

In another embodiment, three-dimensional models of implants may be embedded in a computer library, so that fitting of an implement may be solved by the computer and presented in virtual chronology or "guidepath" that the surgeon may elect to follow when placing the implant. Any interferences and incorrectness of implant size (as would be experienced post-operatively by impingement or ligamentous insufficiency) may be avoided, leading to better outcomes.

Figure 8B:
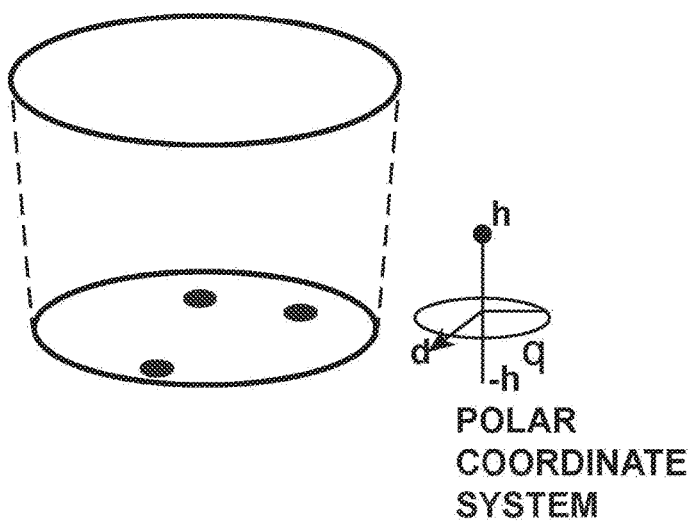
FIG. 8B shows an example data transformation by triangulation to generate an array of polar datapoints.

FIG. 8B shows an example data transformation by triangulation to generate an array of polar datapoints having depth and position. Structured Illumination has the advantage that a polar coordinate system and zero reference point are inherent in the imaging projector and can be used to speed analysis of the remaining mesh map. Data analysis is illustrated schematically in FIG. 8B and generates a dataset having position coordinates and elevation coordinates that can be used to draw a wireframe model and describe a body volume that can then be supplemented with data from one or more internal three-dimensional solid model scans. The combined "fusion 3D model" may then be used to generate projections of virtual images that may be transmitted or piped into the eyepiece for focusing on the retina of the wearer, along with any numerical data or streaming numerical data of relevance to the surgical procedure. Thus, for example, proximity to an artery can be detected by pulsatile pressure on a probe and nerve function can be assessed electrically, extending the range of the surgeon's senses beyond the visual and tactile.

Figure 9:
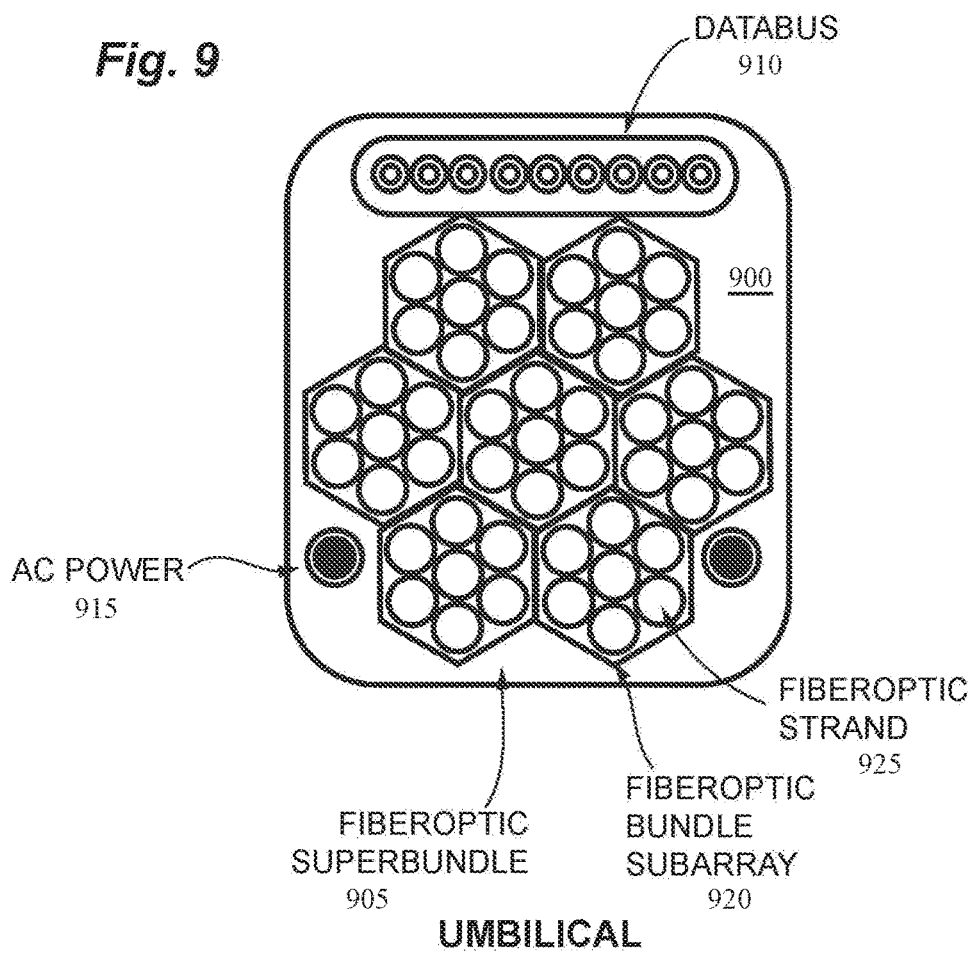
FIG. 9 shows a cross-sectional view of an example umbilicus to a headset by which at least aspects of surgical navigation may be implemented.

FIG. 9 shows a cross-sectional view of an example umbilicus 900 to a headset by which at least aspects of surgical navigation may be implemented, arranged in accordance with at least some embodiments described herein. In this example, the umbilicus 900 provides a fiber optic array 905, a databus 910, and power 915 to the headset 105. Fiber optic bundles 905 may include subarrays 920 of fibers 925 by the thousands as needed to individually paint a surgical field with readily encoded spots. Use of encoded spots may increase hardware costs but may result in significant increases in calculation efficiency and speed, reducing latency in the image refresh rate. A shielded databus 910 is also shown, and while having only an 8-bit bus size (plus parity bit) in this example, may be scaled to include larger parallel bus bundles with a baud rate limited only by the clock frequency of the processors. Fiber optics may also be used for data transmission at GHz speeds, improving system refresh rates and resolution.

Figure 10:
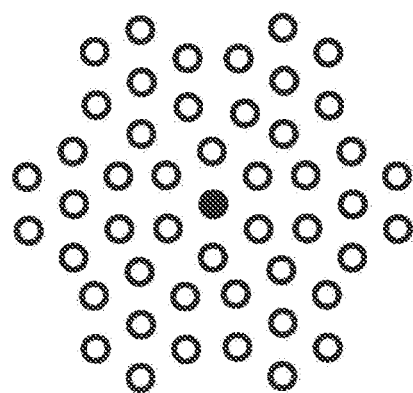
FIG. 10 shows an example dot array by which at least aspects of surgical navigation may be implemented.

FIG. 10 shows an example dot array 1000 by which at least aspects of surgical navigation may be implemented, arranged in accordance with at least some embodiments described herein. In this example, the dot array 1000 may have 60 degree sectoring and a center dot used for rapidly solving the geometry of the spot array and generating a wireframe map.

Figure 11:
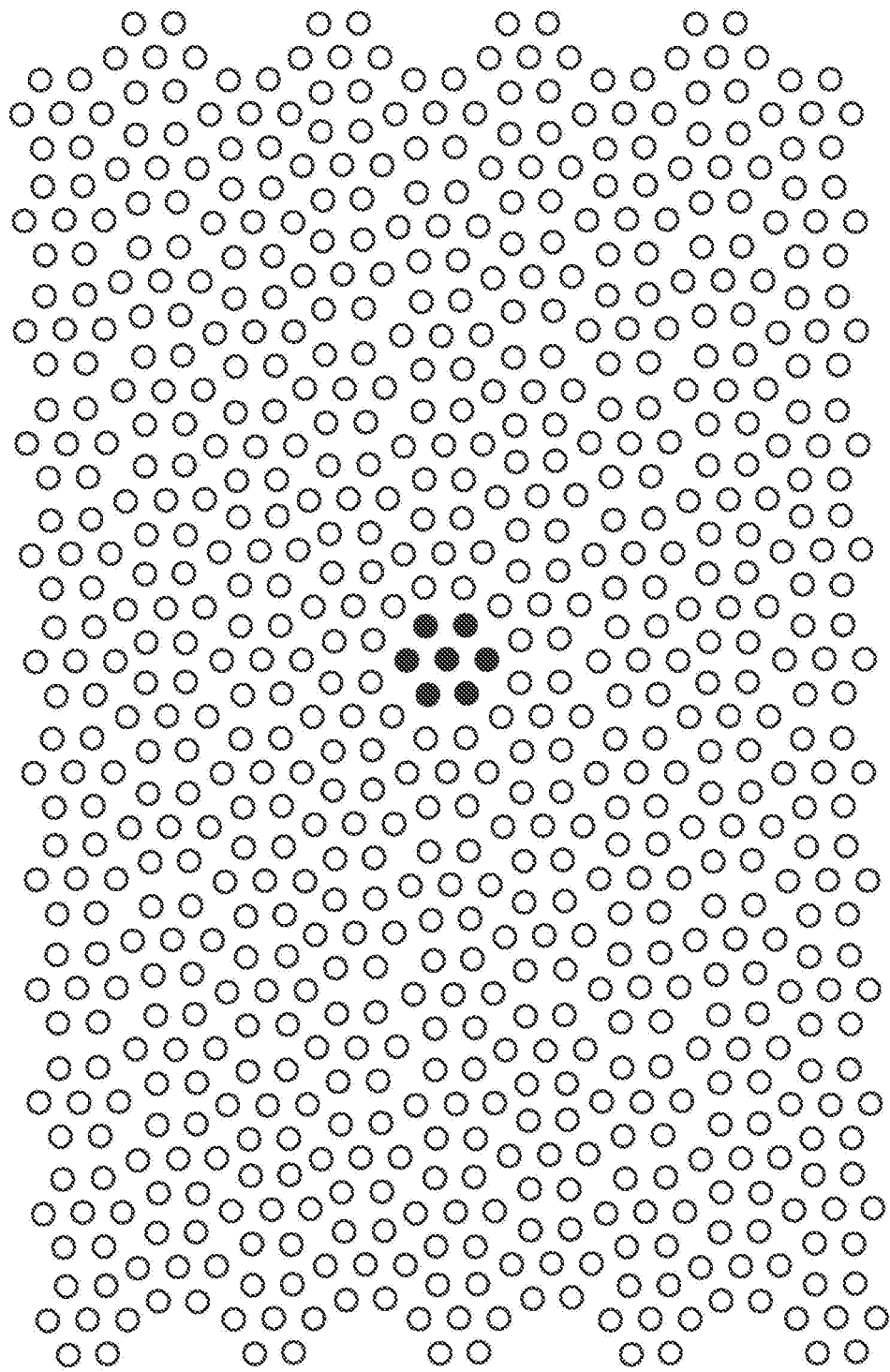
FIG. 11 shows an example structured dot array by which at least aspects of surgical navigation may be implemented.

FIG. 11 shows an example structured dot array 1100 by which at least aspects of surgical navigation may be implemented, arranged in accordance with at least some embodiments described herein. In this example, the dot array 1100 may be scaleable for detailed mapping of a surgical field. The spots may be regularly spaced to improve the speed of geometrical calculations. A wireframe model solution generally propagates from a plurality of known reference points such as the unique hexagon in the center of the field, and leads to coalescence of the entire dot field from multiple centers, as may be derived computationally by using one or more co-processors or parallel processor nodes by computational technologies known in the art.

FIG. 12 shows an example dot array 1200 by which at least aspects of surgical navigation may be implemented, arranged in accordance with at least some embodiments described herein. In this example, the dot array 1200 may have a dot subset for calculating a snap wire frame model. At high speed, a first-pass coarse wireframe model may be constructed from the index dots 1205 (black centers). Then a finishing step may be performed using a more dense dot pattern 1210 (open circles).

A high-speed, large broadband databus may be preferred, but the software for manipulation of the solid model and projection of realistic virtual images is designed to reduce the computational workload using structured light in one embodiment. Speckled light may be used in other embodiments, consisting essentially of generally irregular dot patterns projected by imprecise optical trains, but those skilled in the art will recognize that a corresponding increase in computational load may result due to the need for error correction and more probabilistic algorithms for assigning datapoints in building comparative maps from two synchronous camera frames taken from different angles. Use of a dual framegrabber and software capable of assigning dot pairs $(x_1 y_1 z_1, x_2 y_2 z_2)$ from the two frames based on frequency encoding may accelerate the needed triangulation to construct a depth map and correlate that with a live camera view. Subsequent processing may be done by raytrace software or equivalent means for generating a fusion virtual image that may be projected onto the eyepiece with a selectable level of transparency of the virtual features. The user can select a fully transparent view of the solid model, a view that is transparent only where a surgical incision is made (or about to be made), or an opaque view that shows only the external image.

Advantageously, by using a cluster of laser emitters in combination with a beam splitter that divides the output among multiple fiber optic strands, patterns of spots having multiple frequencies can be formed into a quilt, where the frequencies may be encoded to accelerate solution of the three-dimensional geometry. Once the dot array is solved, motion of the headset may be tracked using accelerometry or motion relative to fixed reference points, and the dot array may be refreshed accordingly so that raytracing of the virtual image is always aligned according to the perspective of the user and is anatomically correct.

The software can learn reference points defined by the user, either by marking those spots with a laser pen, or using radiobeacons placed for example at major boney crests. The software can also recognize underlying fascia surrounding the spinous process of each vertebral body, for example, after a first incision is made and the cut retracted, so that the three-dimensional solid model may be correctly aligned relative to the patient's anatomy on the operating table. Other anatomical reference points are well known to physicians and may be entered using a combination of a voice identifier and a laser pointer, for example. Alternatively, RFID pads may be adhered to anatomical landmarks surrounding the surgical site, providing a means to align the solid model with the patient's position on the table even when visual cues are temporarily blocked.

Figure 13A:
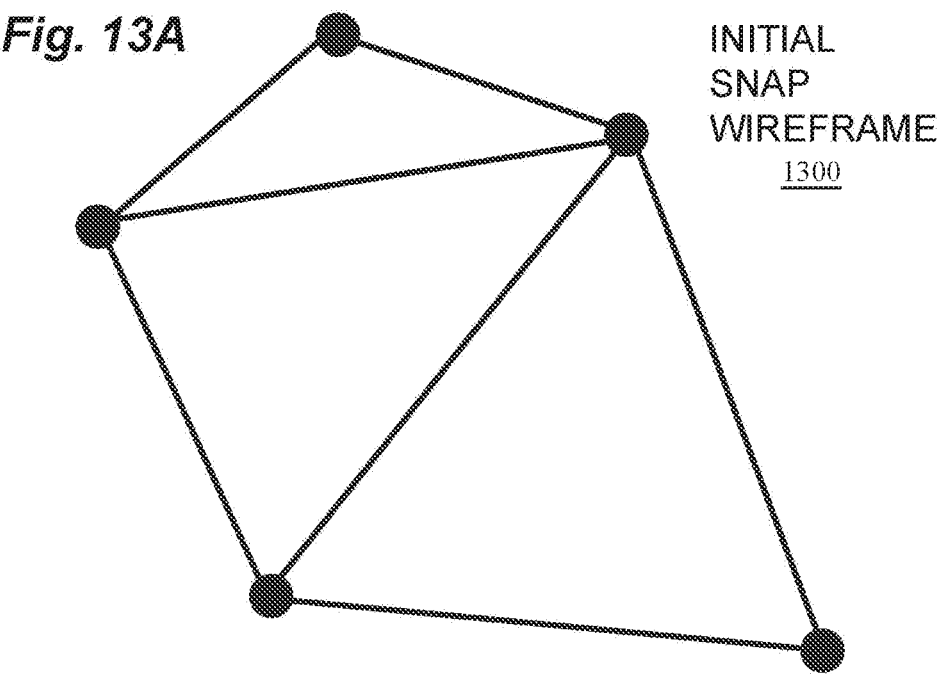
FIG. 13A shows an example snap wireframe model by which at least aspects of surgical navigation may be implemented.
Figure 13B:
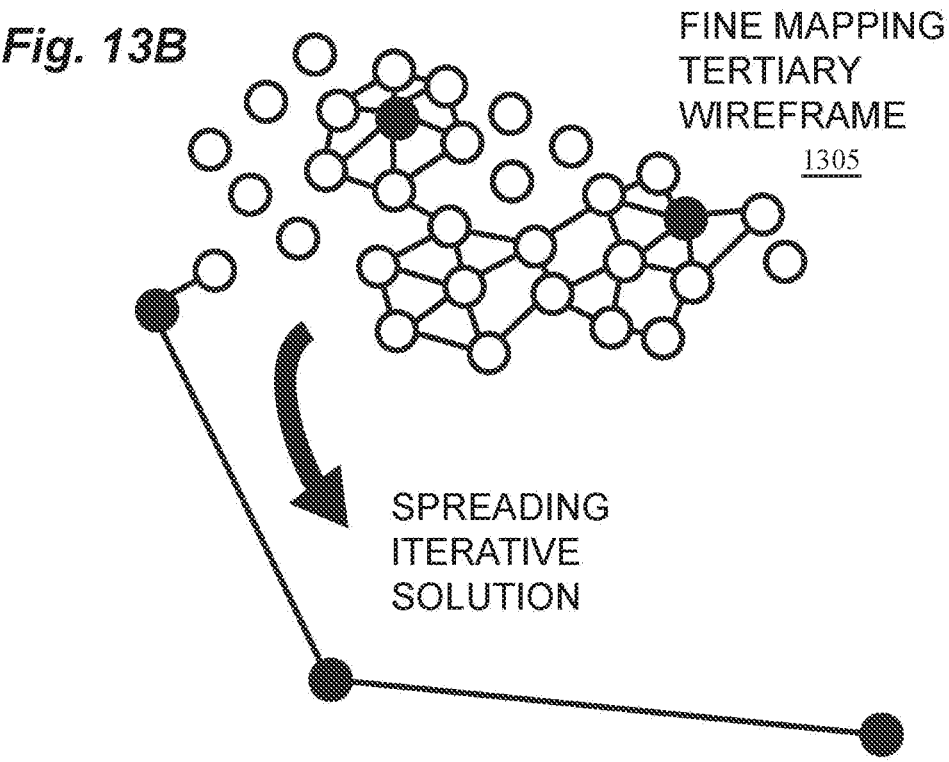
FIG. 13B shows an example tertiary wireframe model by which at least aspects of surgical navigation may be implemented.

FIG. 13A shows an example snap wireframe model 1300 by which at least aspects of surgical navigation may be implemented, arranged in accordance with at least some embodiments described herein. Similarly, FIG. 13B shows an example tertiary wireframe model 1305 by which at least aspects of surgical navigation may be implemented, arranged in accordance with at least some embodiments described herein. FIGS. 13A and 13B together represent steps for creating the snap wire frame model 1300 and building the detailed model 1305 from the skeletal array of the first step. The propagation of the fine mesh model may occur from multiple centers and may coalesce in a complete map. Advantageously, areas of the map that are unchanged may be bypassed when refreshing the fusion three-dimensional solid model and downstream virtual images streamed to the headset.

Figure 14A:
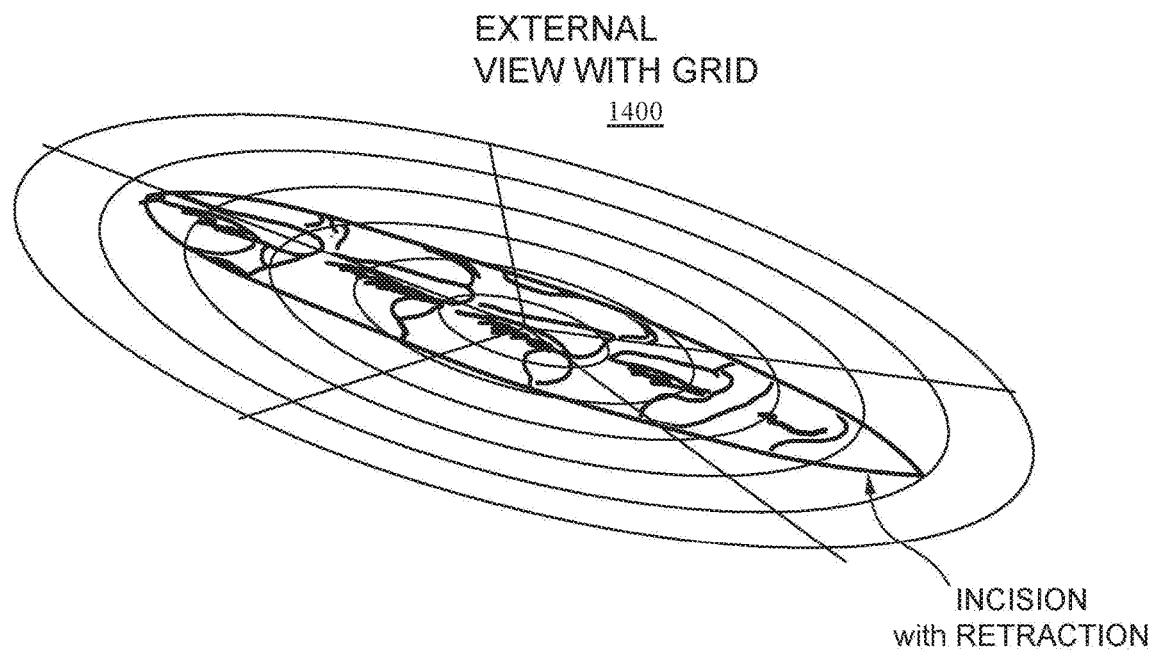
FIG. 14A shows an example headset view having a polar grid for mapping a surgical field by which at least aspects of surgical navigation may be implemented.

FIG. 14A shows an example headset view 1400 having a polar grid for mapping a surgical field by which at least aspects of surgical navigation may be implemented, arranged in accordance with at least some embodiments described herein. In this example, the headset view 1400 provides a conceptual polar grid for rapidly mapping a surgical field and for building a three-dimensional fusion model incorporating CT data as projected into virtual images displayed in the eyepiece of the headset 105.

Figure 14B:
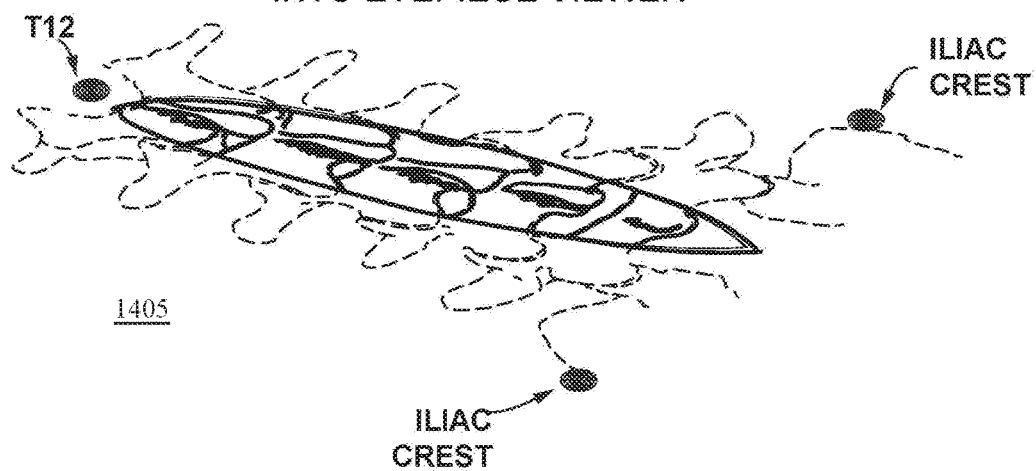
FIG. 14B shows an example virtual fusion model by which at least aspects of surgical navigation may be implemented.

As shown in FIG. 14B, the resultant three-dimensional fusion model 1405 is Analogous to "X-ray vision" and allows the surgeon to visually inspect, for example, the overlying tissues, incision, and the underlying vertebra, shown here as an open window to the lumbar spine. As before, radiobeacons or optical beacons may be used to supplement the view and improve the speed of image re-integration following interruptions in the data stream such as by movement of an arm through the field or a glance up to the wall clock. But then, the eyepiece may also include a display of a time indicator, so the physician is less likely to be distracted during critical steps of the operation.

Figure 15A:
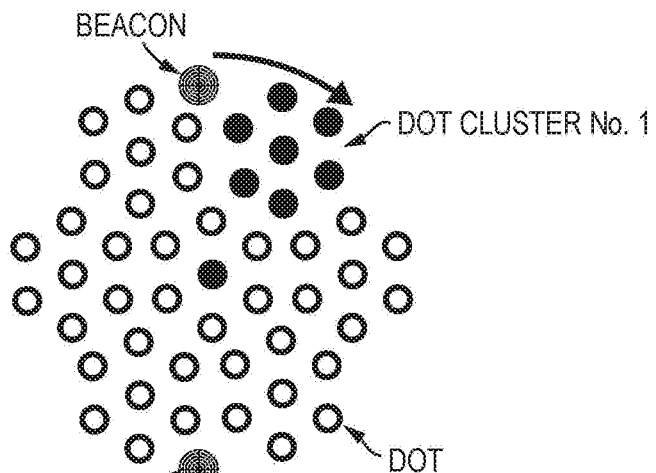
FIGS. 15A-15C show an example strobe sequence by which at least aspects of surgical navigation may be implemented.
Figure 15B:
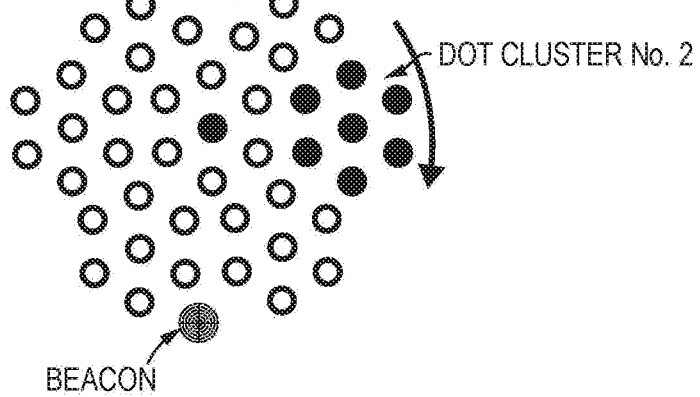
Figure 15C:
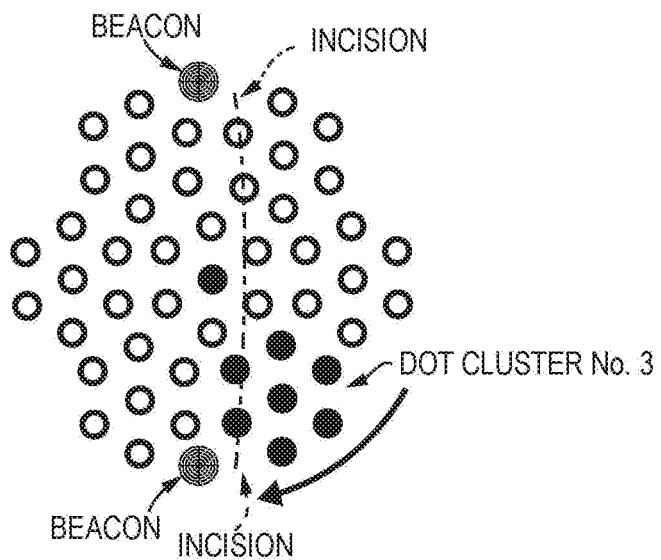

FIGS. 15A-15C show example views of a strobe sequence whereby dot data may be presented to the processor in sectors. Beacons may be used to add supplemental confirmatory arthrospatial datapoints. RFID chips or hybrid reflector/radio tags may also be used. Tags having prismatic colored surfaces may also serve as unique arthrospatial locators that supplement the patterned projection.

FIGS. 16A and 16B show a two-page example process flow 1600 for building a three-dimensional virtual fusion view by which at least aspects of surgical navigation may be implemented, arranged in accordance with at least some embodiments described herein. In this example, data processing steps are shown for rapidly building a detailed three-dimensional virtual model starting from a snap wireframe of a data subset (Step 1). In Step 2, two frame grabbers are used to capture an instantaneous view of an encoded dot pattern that is pulsed on a surgical field. The cameras may be synched to the projector and between pulses acquire native RGB views that can be used to enhance the quality of the virtual images and to subtract background light. In Step 3, the two camera frames are used to draw a correlation map based on images of the spots; more than one filter may be used to selectively acquire certain frequencies in rapid succession so as to collect the encoded spot data. Each frequency set helps to rapidly construct a coherent pattern across the entire surgical field. In Step 4, a correlation model is assembled, the model consisting of a database having data fields, each data field having a position and an elevation that may be used to draw a wireframe or "mesh" model from which anatomical features and a body solid outline may be identified. In Step 5, the wireframe model and a reference 3D solid model (such as from a CT scan) may then be processed by data fusion processing as known in the art to produce a virtual solid model, termed here a "fusion 3D model" that extends from the surface of the surgical field to any internal structures observable in the CT scan, as correctly registered according to the body position and observable anatomical features that were captured in the earlier step. If needed, beacons may be used to assist in registration, or an instruction subroutine may be run where a surgeon points out the relevant registration guides on the external wireframe model and in the CT solid model so that the computer may propagate the alignment and generate virtual views of the model for projection into the eyepiece (Step 6), where the images may be further lensed if needed so as to be correctly portrayed on the retina of the wearer.

The process is iterative. As shown in FIG. 16B, the process repeats as a loop. Step 1 pulses a dot pattern on the surgical field. In Steps 2 and 3, reflections (any light returning to a camera lens) are then mapped. In Steps 4 and 5, anatomical landmarks are identified in a wireframe model of the surgical field and the dataset is fused with a three-dimensional solid model. In Step 6, the "fusion 3D model" that results is then used to generate virtual images for projection onto the eyepiece of the headset. In Step 7, the process then returns to a "START" (FIG. 16A) and begins again according to a clock speed and a data transmission rate. The process may be repeated at a speed sufficient to assist the surgeon and validate surgical intuition and direct observation during the surgical procedure.

In advanced steps, surgical instrumentation may also be tracked, and geometric calculations needed to orient and properly perform surgical steps may be shown in virtual tracks projected onto the virtual fusion image, tracks that are visible only through the headset eyepiece.

Figure 17:
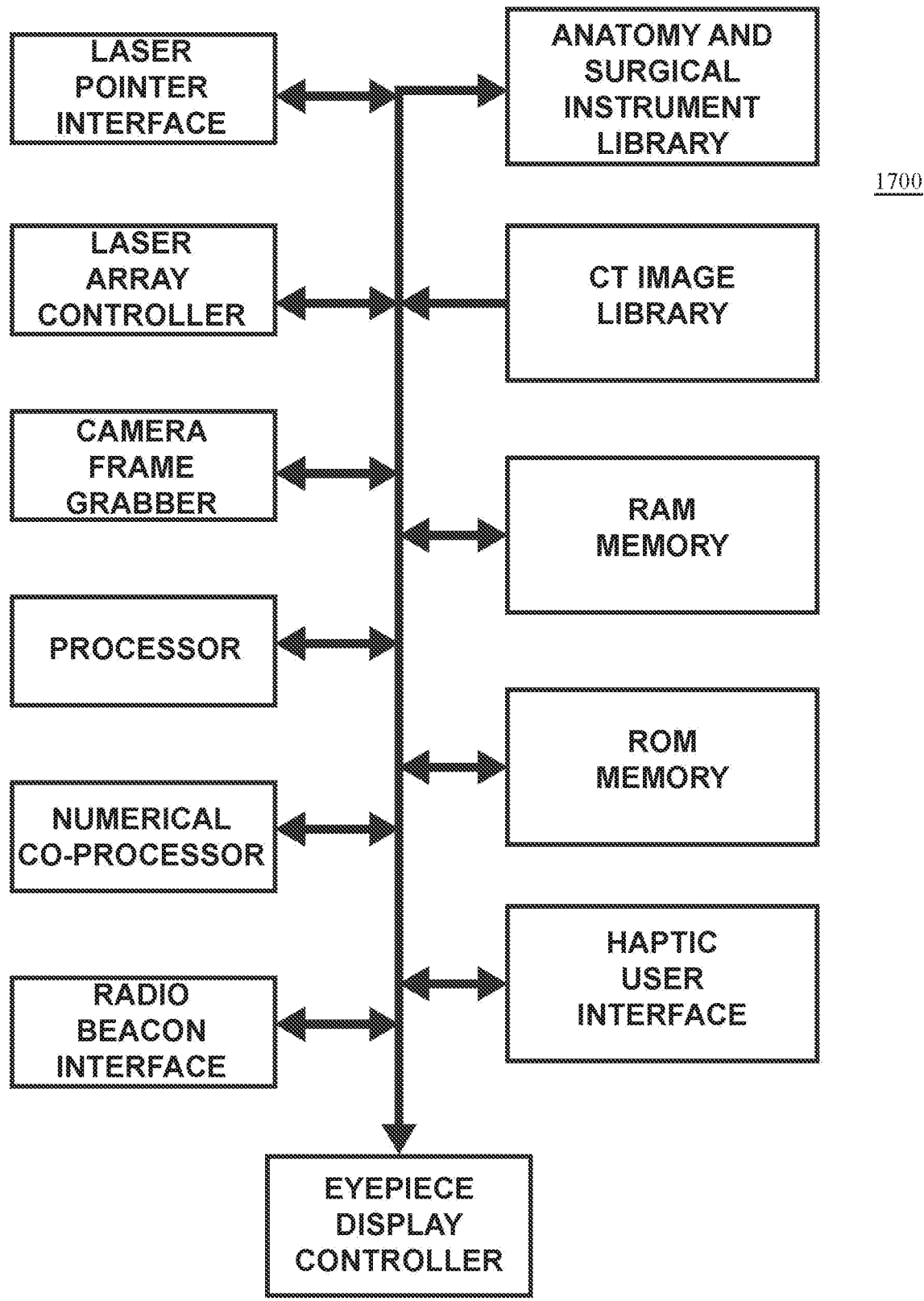
FIG. 17 shows a block diagram of an example computing system by which at least aspects of surgical navigation may be implemented.

FIG. 17 shows a block diagram of an example computing system 1700 by which at least aspects of surgical navigation may be implemented, arranged in accordance with at least some embodiments described herein. In this example, computing system 1700 includes a computing machine and peripherals dedicated for rapidly building detailed three-dimensional virtual models of a surgical field with an embedded three-dimensional solid model stored in a library and derived from 3D X-ray, CT, MRI or other imaging modality. Provision for representing a library of surgical instruments in the eyepiece is also provided. Similarly, prosthetic implant solid models may also be referenced from a database if required.

As mentioned, advantageously, the techniques described herein can be applied to any device. It can be understood, therefore, that handheld, portable and other computing devices, systems, networks, and computing objects of all kinds (including robotics) are contemplated for use in connection with the various embodiments. Accordingly, the general purpose remote computer described schematically in FIG. 17 is but one example of a computing device.

FIG. 17 thus illustrates an example of a suitable computing system environment in which one or more aspects of the embodiments described herein can be implemented. Components of the computer machine may include, but are not limited to, a processing unit, a system memory, and a system bus that couples various system components including the system memory to the processing unit.

Computers as shown typically include a variety of computer-readable media that can be any available media that can be accessed by computer. The system memory may include computer storage media in the form of volatile and/or nonvolatile memory such as read only memory (ROM) and/or random access memory (RAM). By way of example, and not limitation, system memory may also include an operating system, application programs, application program interfaces, other program modules, and program data, including databases and library data.

A user can enter commands and information into the computer through input devices termed here as "interfaces". The eyepiece display module or other type of graphical display device may also be connected to the system bus via an interface, such as an output interface. In addition to a monitor, computers may also include other peripheral output devices such as speakers, which may be connected through an output interface. A microphone may also be included whereby the computer may respond to verbal commands. A haptic interface may also be utilized by the system.

The computer may operate in a networked or distributed environment using logical connections to one or more other remote computers, such as remote computer. The remote computer may be a workstation, a personal computer, a server, a router, a network PC, a peer device or other common network node, or any other remote media consumption or transmission device, and may include any or all of the elements described above relative to the computer. The logical connections depicted in FIG. 17 may include a network, such as a local area network (LAN) or a wide area network (WAN), but may also include other networks/buses. Such networking environments are commonplace in homes, offices, enterprise-wide computer networks, intranets and the Internet and are cited only as examples of the kinds of digital environments that may support the system.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

Figure 18:
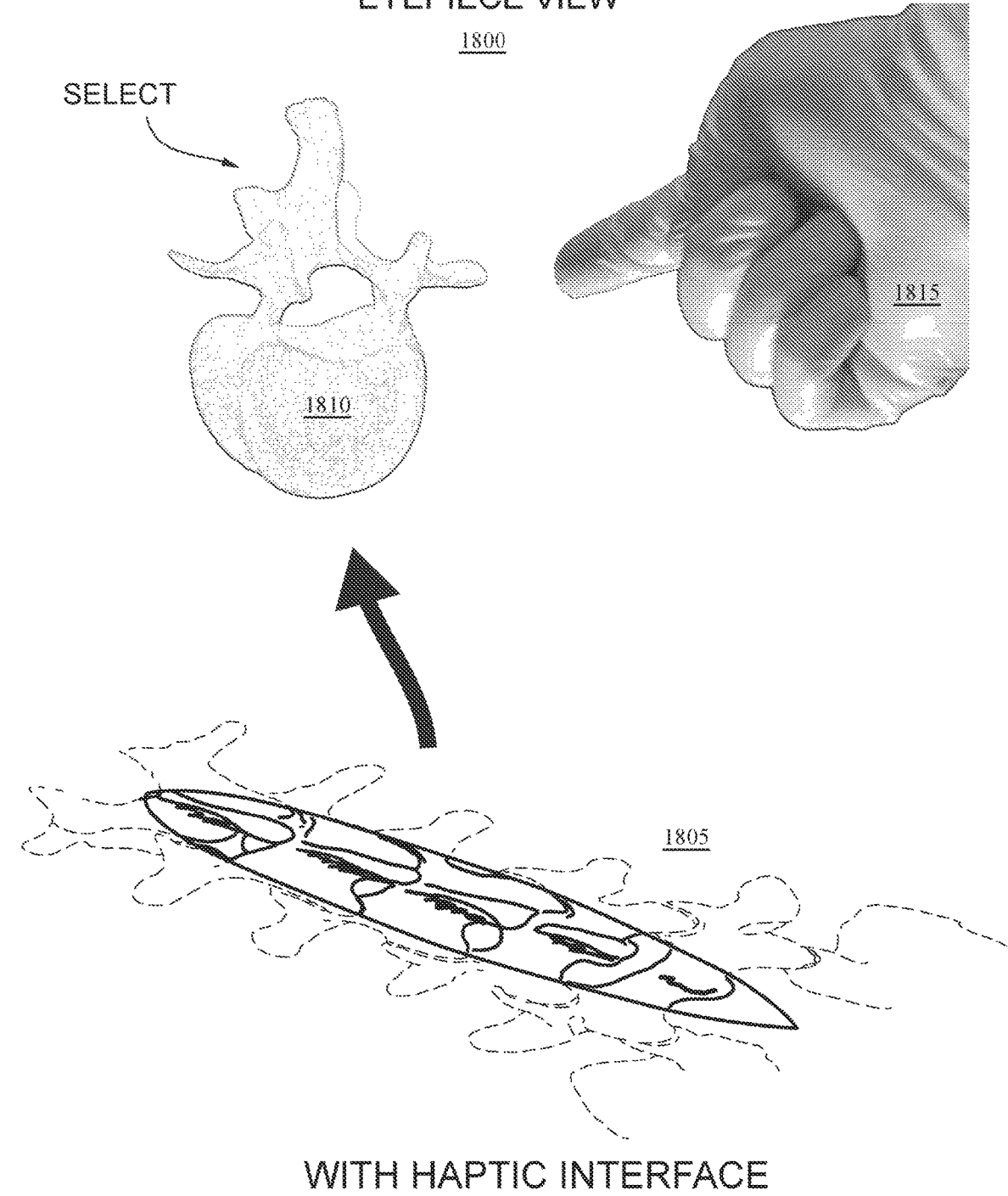
FIG. 18 shows an example headset view of a select command by which at least aspects of surgical navigation may be implemented.

FIG. 18 shows an example headset view 1800 of a select command by which at least aspects of surgical navigation may be implemented, arranged in accordance with at least some embodiments described herein. In this example, the headset view 1800 shows a surgical field 1805 with a virtual object 1810 projected in the eyepiece above the incision site. The gloved hand 1815 is used to manipulate the virtual object 1810, as shown in the following views. In this example, the surgeon's finger is used to select a vertebra from anatomical features visible through the incision. A virtual solid model of vertebra L3 is projected in the eyepiece using raytrace software so as to appear to hang above the surgical field. Osseous features such as a fractured pedicle, and soft tissue detail (such as a nerve pinch, disk bulge, and Doppler flow) may be represented as needed to assist the surgeon using data fusion and segmentation of multiple imaging inputs. Data from probes having sensory outputs, such as temperature, bone density, EKG, myelography, and EEG may also be displayed in the headset eyepiece.

FIG. 19 shows an example headset view 1900 of a levitate command by which at least aspects of surgical navigation may be implemented, arranged in accordance with at least some embodiments described herein. In this example, the headset view 1900 shows a simple haptic command by which the surgeon can raise a virtual object 1905 to eye level for closer inspection. A virtual vertebra is abstracted from a CT scan in this example; the view of the surgeon's hand may be integrated from a camera in the headset. Structured light cast on the hand may be sufficient to accurately detect and encode hand gestures by modeling the hands as a function of time in the viewing field. Radio reflective dots or RFID chips may be included inside the gloves near the fingertips so as to make this process faster.

Figure 20:
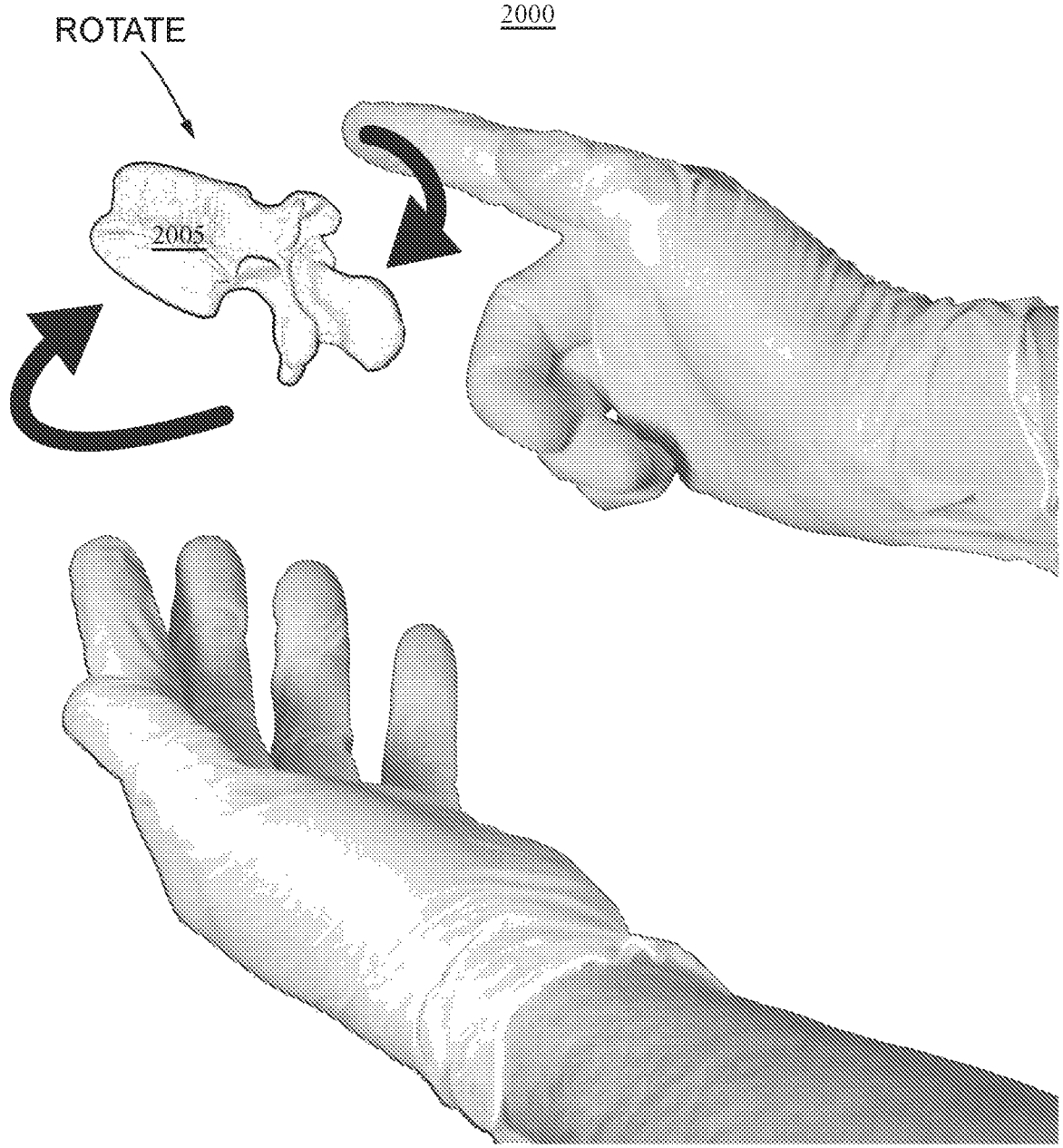
FIG. 20 shows an example headset view of a rotate command by which at least aspects of surgical navigation may be implemented.

FIG. 20 shows an example headset view 2000 of a rotate command by which at least aspects of surgical navigation may be implemented, arranged in accordance with at least some embodiments described herein. In this example, the headset view 2000 shows a haptic rotate command by which a vertebral body 2005 may be instructed to rotate or turn over according to the motion of an index finger. When a suitable view is found, the user may form a first to freeze the image.

Figure 21:
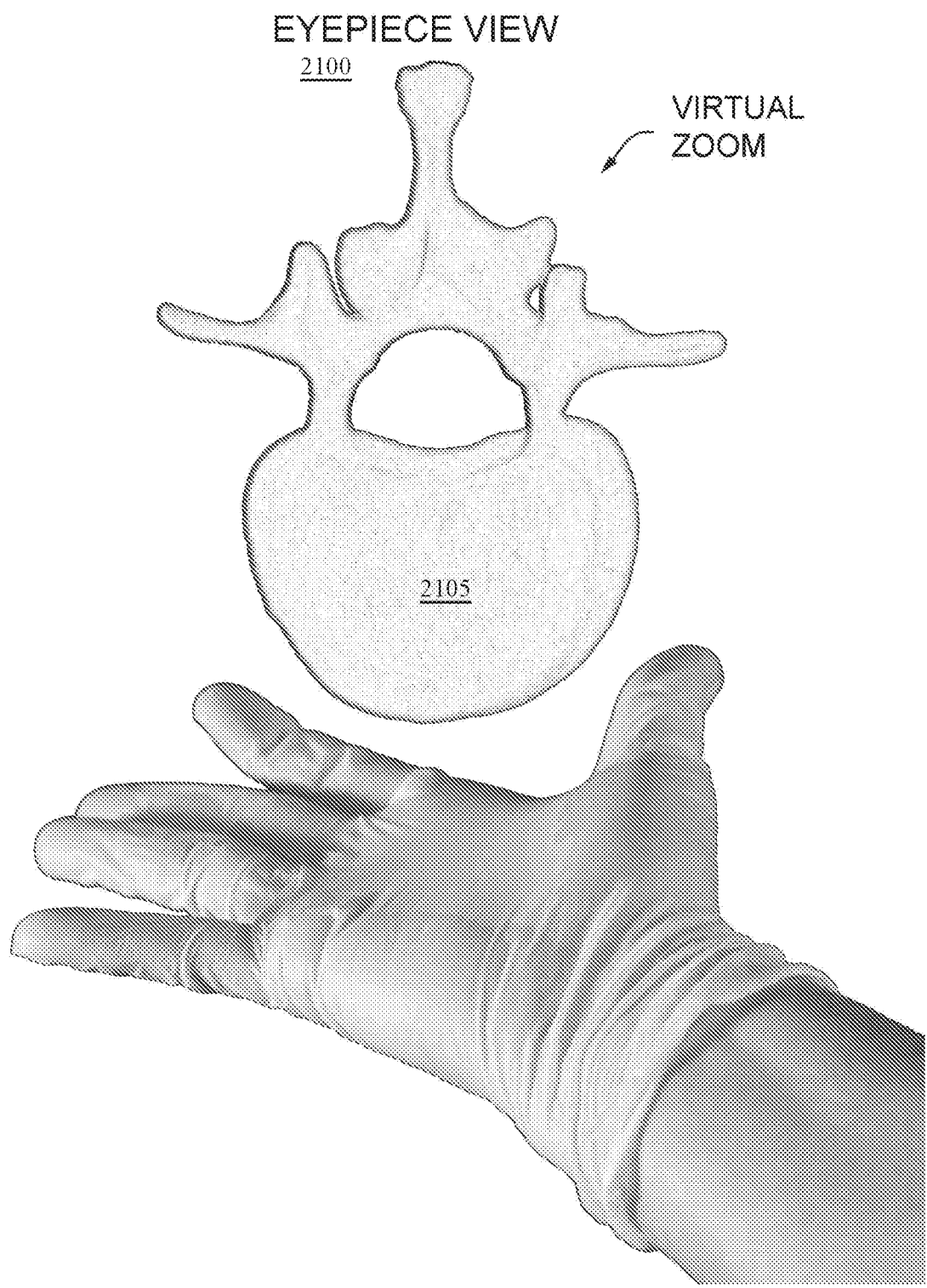
FIG. 21 shows an example headset view of a zoom command by which at least aspects of surgical navigation may be implemented.

FIG. 21 shows an example headset view 2100 of a zoom command by which at least aspects of surgical navigation may be implemented, arranged in accordance with at least some embodiments described herein. In this example, the headset view 2100 shows a haptic zoom command, where the virtual image 2105 may be positioned and expanded as displayed in the surgeon's eyepiece. The enhanced size aids in detecting any pathology and in visualizing angles and other dimensions. Data may be streamed to the eyepiece for instant reference and may be updated in real time as the surgeon indicates relevant features of interest.

Figure 22:
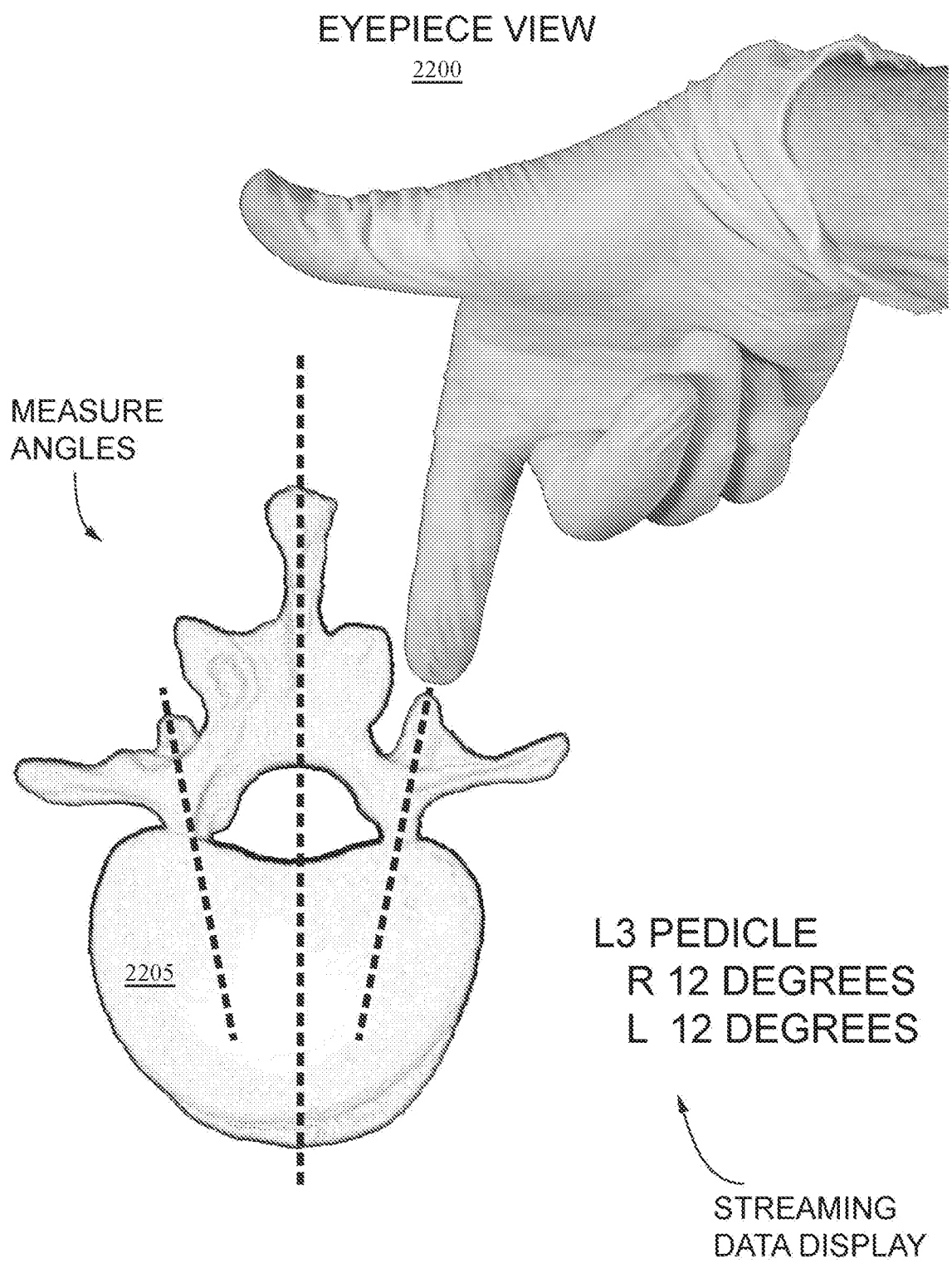
FIG. 22 shows an example headset view of an angle measurement command by which at least aspects of surgical navigation may be implemented.

FIG. 22 shows an example headset view 2200 of an angle measurement command by which at least aspects of surgical navigation may be implemented, arranged in accordance with at least some embodiments described herein. In this example, the headset view 2200 shows another haptic command, here a thumb and forefinger gesture indicating that the computer is to calculate and plot angles of relevant anatomical features of a vertebral body 2205. Streaming data may accompany the image. An alternate gesture may be a scissors motion, in which the surgeon points at a relevant feature and then scissors the index finger and middle finger to indicate that angles are to be displayed.

Figure 23:
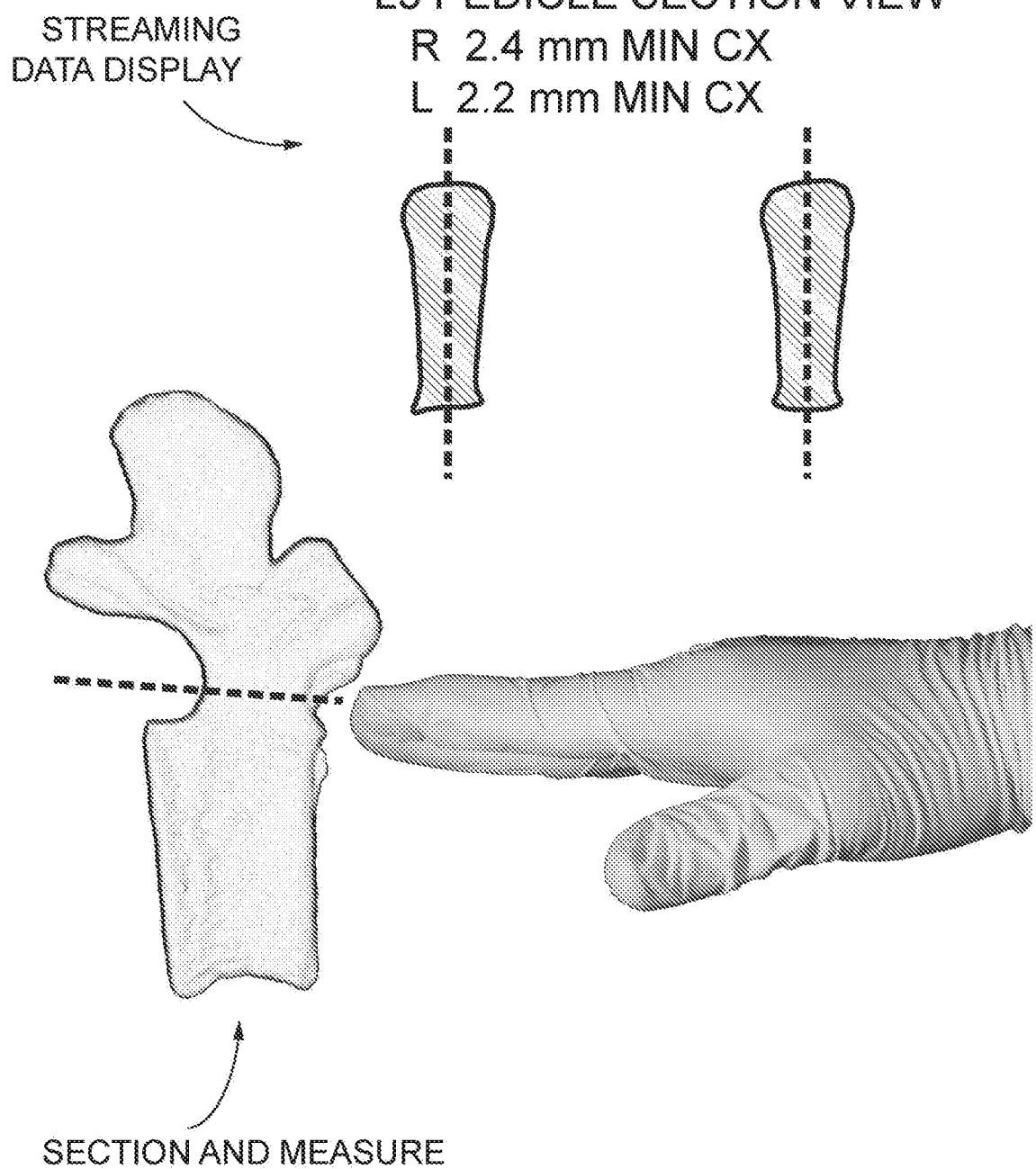
FIG. 23 shows an example headset view of a slice command by which at least aspects of surgical navigation may be implemented.

FIG. 23 shows an example headset view 2300 of a slice command by which at least aspects of surgical navigation may be implemented, arranged in accordance with at least some embodiments described herein. In this example, a graphical interface may be programmed to show the slice in cross-section, and the slice may be repositioned by moving the hand up or down. Also shown are relevant dimensions, such as the thinnest cross-sectional dimension of the right and left pedicles, as tabulated here. While the surgeon may use an enlarged virtual image for finer detail, the actual dimensions and angles reported may be as found in vivo, vis a vis the patient's skeleton.

Figure 24:
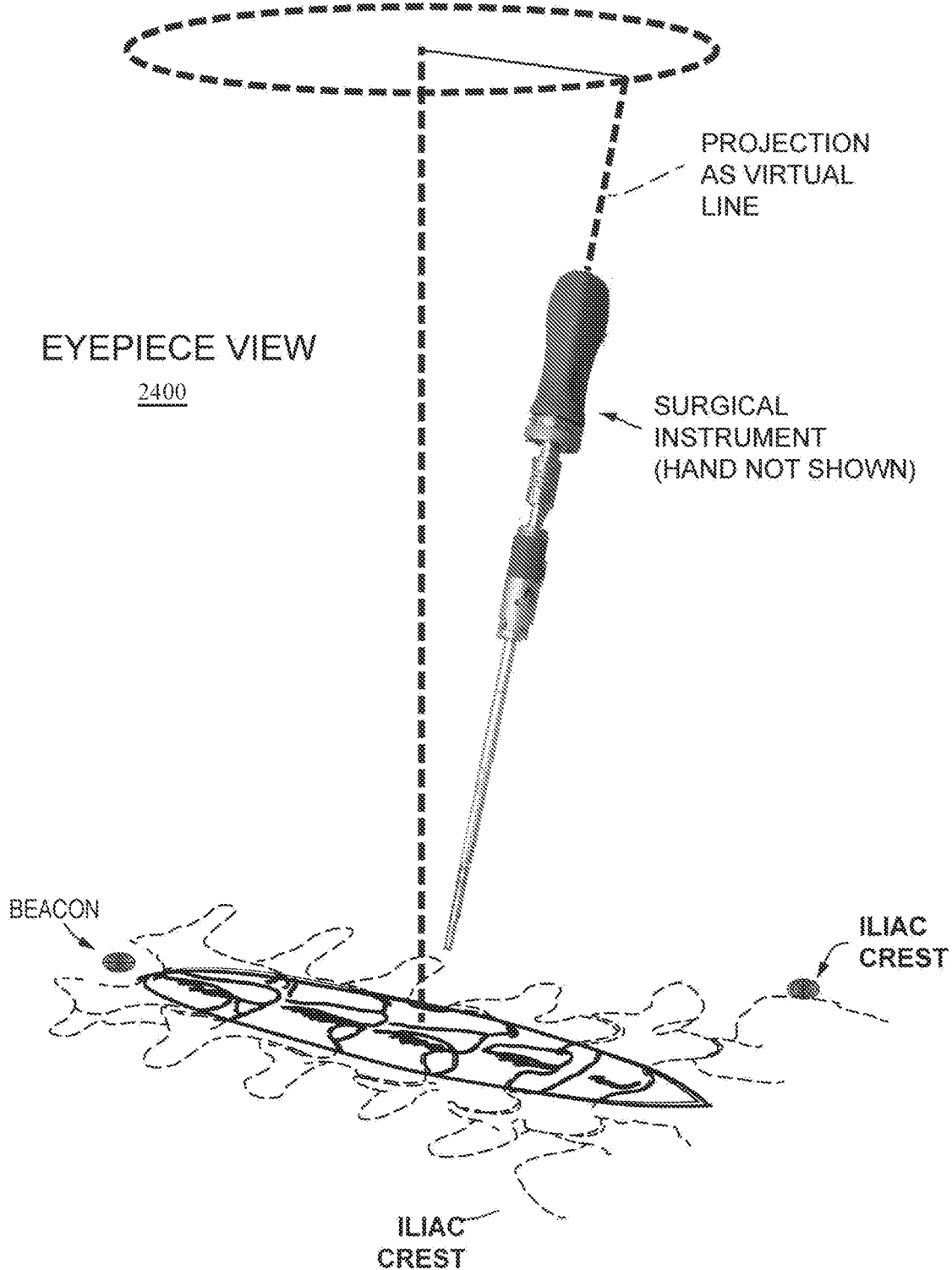
FIG. 24 shows an example headset view of surgical instrument positional analysis by which at least aspects of surgical navigation may be implemented.

FIG. 24 shows an example headset view 2400 of surgical instrument positional analysis by which at least aspects of surgical navigation may be implemented, arranged in accordance with at least some embodiments described herein. In this example, FIG. 24 shows that along with anatomical features, a database of surgical instruments, hardware, and prosthetics (implants) may also be shown in the eyepiece and manipulated along with positional analysis in real-time. Data may be streamed to the eyepiece to assist in accurate placement of surgical screws and K-wires, for example. These views may be supplemented by "in suite" views taken during the surgery using a fluoroscope or other active imaging modality. AP and Lateral views are commonly used to guide and assess placement, but the system may supply active guidance and may integrate X-rays by best-fit image analysis processes in order to update the solid model. Shown again here are radiobeacons useful in updating the wireframe model and solid model fusion if needed, and for maintaining a live view in virtual mode when there is visual obstruction. Alternatively, instruments may be monitored and tracked using optical or electrometric technology as described in US Pat. Doc. Nos. 2005/0228270 and 2013/0267833, which are hereby incorporated by reference.

Alternatively, a surgical plan may be used to generate a series of reference views or a video, such that a guidepath for insertion of a screw or an implant may be superimposed on the live view of the surgical site during the surgical procedure. Robotic steps may also be guided in this way.

Importantly, by using high quality visual clues to simulate increasing depth and intervening overlayers, the physician's intuitive sense of position and structure is enhanced, not interfered with. Deep structures may be shown, for example, in pale lime green shades that fade with depth so as to be readily distinguished from the red and white structures of the exterior view. Vectored raytrace algorithms may be useful for showing features in perspective to enhance a sense of depth. Special preference may be given to showing information by relevance, so that distracting parts of the field are not shown. For example, the anatomy around a vertebral screw tract may be shown, but not the superjacent and subjacent vertebra, which could clutter the field. In another example, the anatomy of the tibia and fibula may be shown with an axial centerline when drilling a guide hole and shelf in preparation for mounting a prosthetic on the tibial plafond. Deviations above and below, as well as medially and laterally from the centerline may be highlighted by projecting a comparative divergence angle between the true centerline and the projected drill centerline or blade cut. In this way, costs for revision surgery may be reduced or avoided. In another example, ligament balance and gait analysis may also be projected during the surgery to improve outcomes, but views of the metatarsals, navicular, and calcaneus may be hidden during surgery on the ankle joint unless summoned or contextually relevant to the procedure so as to avoid clutter. In another example, a virtual mirror may be summoned to show the underside view when operating a saw that would otherwise obstruct oversight of the cut.

Figure 25A:
FIG. 25A shows an example unaided view of surgical gloves.
Figure 25B:
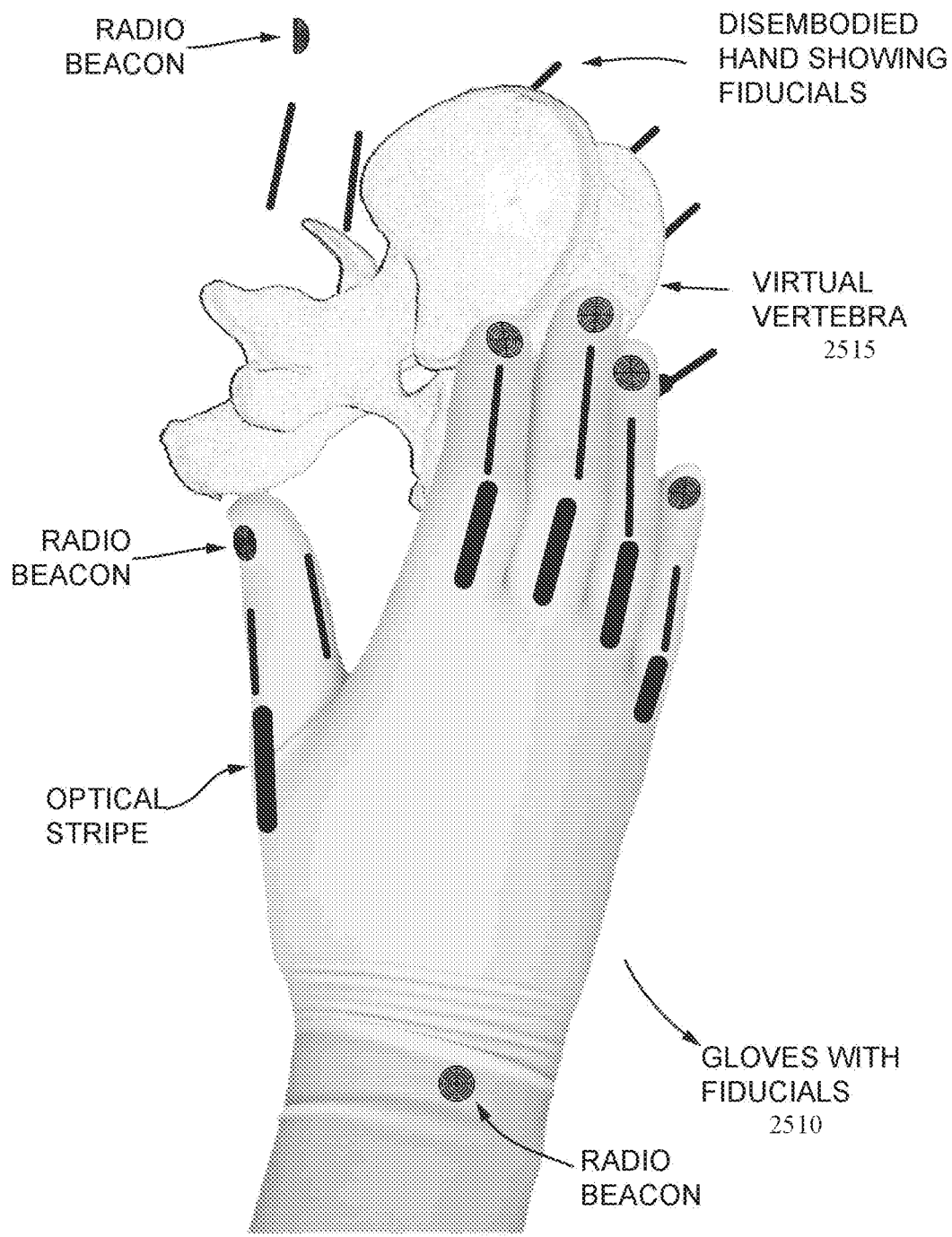
FIG. 25B shows an example headset view of a visible surgical glove manipulating a virtual object.
Figure 25C:
FIG. 25C shows an example headset view of an invisible surgical glove manipulating a virtual object.

FIGS. 25A, 25B and 25C are different views of surgical gloves by which at least aspects of surgical navigation may be implemented, arranged in accordance with at least some embodiments described herein. FIG. 25A shows an example unaided view 2500 of surgical gloves. FIG. 25B shows an example headset view 2505 of a visible surgical glove 2510 manipulating a virtual object 2515. FIG. 25C shows an example headset view 2520 of an invisible surgical glove manipulating a virtual object.

In these examples, the gloves may be visualized using a projected dot matrix if desired. Alternatively, the gloves may be modified with a registration stripe on each finger, and optionally an RFID antenna tag near the fingernail of each finger and on the boney prominence of the scaphoid bone, medial and distal to the radius at the wrist so as to quickly convey a gesture command language. For more detail, the hands of the surgeon may be separately segmented from the remainder of the image using a blue, violet or ultraviolet dot matrix projector on the headset in combination with a bandpass filter in the near visual and ultraviolet range. This segmented model may not automatically be incorporated into the virtual augmentation presented to the eyepiece display, but may be used by the computer to track the motion of the hands for gesture recognition and when needed for selectively making the hand visible in the virtual view or invisible. In some instances, the hand may be an obstruction, so it may be desirable that the hand be visible to the unaided eye but not seen in the augmented eye. One or both hands may be made invisible following digitization and corrective raytrace rendering of the underlying anatomy. By hand, the attached arm may also be subject to selective display.

Relevant art includes U.S. Pat. Doc. No. 2002/0198472 to Kramer and U.S. Pat. No. 7,662,113 to Pearl. These patent documents are hereby incorporated by reference.

Similarly, surgical tools and prosthetics may be selectively segmented more rapidly by use of an alternate dot matrix. Motion dramatically increases complexity of the calculation set required to render the hands and the tools, so the conical narrow beam of the headset may be more dense than a general pattern of dots covering the surgical field. By projecting a blue, violet or ultraviolet dot matrix to model the surgeon's hands and tools, and an IR dot matrix to model the patient's body form and any surgically exposed bones or soft tissues, specialization of function dramatically increases the speed at which calculations can be made without interference or cross-talk. An advantage is that the segmented components can then be selectively displayed in the eyepiece. For example, the hand may be holding a tool but only the tool is shown so that the underlying anatomy is not obstructed. Surgeons can use their unaided eye to follow the tool, but can also see the underlying solid model in the augmented eye and can follow a projected guidepath to the target surgical site, such as a screw hole through a pedicle of a vertebra or into the head of the humerus, for example.

Figure 26:
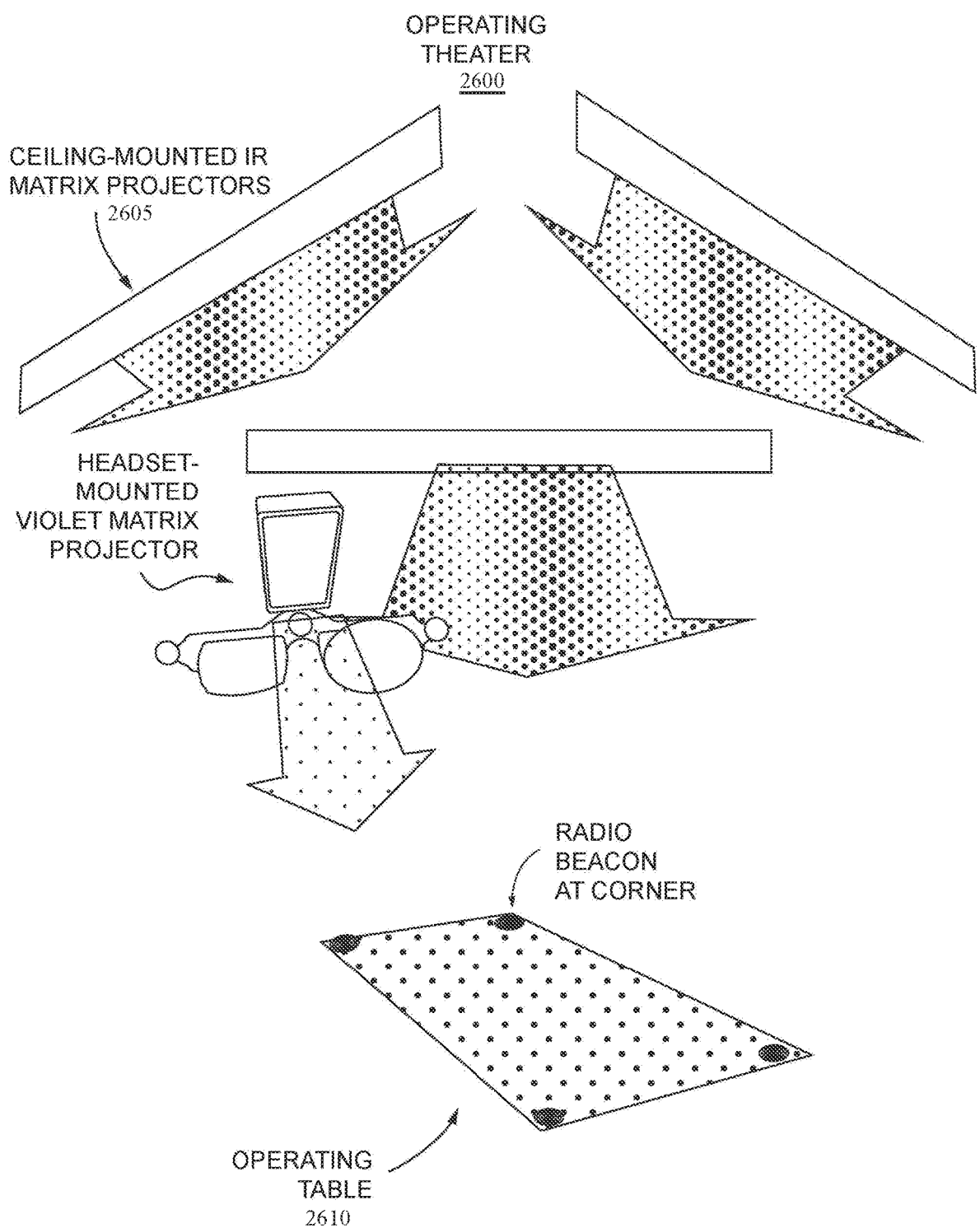
FIG. 26 shows a schematic representation of an example operating room having projection systems by which at least aspects of surgical navigation may be implemented.

FIG. 26 shows a schematic representation of an example operating room 2600 having projection systems by which at least aspects of surgical navigation may be implemented, arranged in accordance with at least some embodiments described herein. For example, a surgical suite with a more complex surgical navigation system is shown. Two dot-pattern projection systems, one that is ceiling mounted and another that is headset mounted, are provided. In this view, the system includes hardware built into the headset 105 and the operating room 2600.

The headset 105 may include the following components: a dot matrix projector (wavelength in blue or violet at fringe of visual range, optionally in UV range outside of UVA and UVB regions); bilateral cameras (2×2) with dual bandpass filter and CCD; radio receivers (right/center/left) for rough triangulation and image updating as headpiece moves; eyepiece with display and lensing (termed here the "eyepiece"); eye pupil camera for fine adjustment of display in eyepiece; and fixed laser pointer.

The eyepiece may be configured to supply virtual images to one eye of the surgeon. The brain of the surgeon provides the needed "wetware" to integrate these images into the corresponding view through the unaided eye, if the images are correctly aligned. If needed, a camera may also be provided in the headset to monitor eye movements, pupil position and lens curvature of the unaided eye so as to project a biocompatible virtual display into the augmented eye, a virtual display that can be shared by both hemispheres of the brain and by the motor cortex and cerebellum without disorientation or confusion. Generally, this can be achieved by modeling of the perspective as seen by the unaided eye, and modeling that perspective in virtual renderings using raytrace software for the augmented eye display.

The operating room 2600 may include IR dot projectors 2605 from multiple sides of the ceiling (existing hardware) having at least three banks to project a superimposed dot matrix from multiple angles, preferably at 60 degree stations or at 90 degree stations relative to the surgical field so as to eliminate or reduce "blind" spots in the dot pattern.

Dot reflections may be captured by at least two cameras mounted on the surgical headset and may be digitized for processing by an external computer as presently conceived. A frame grabber synchronizes the capture of images from each camera and the frames may be compared to map a wireframe model of the surgical site. Reference landmarks may be identified or may be taught to the computing machine by using a laser pointer or a finger plus voice commands. Once properly aligned, fusion software may be used to orient a solid model of the patient anatomy onto the wireframe model of the surgical field. Segmented solid model libraries may contain individual bones, organs, or soft tissue elements. The libraries may also include surgical tools and libraries of prosthetics and surgical hardware.

Surgical tools may include at least two radio antennae wrapped around a stem of the tool so as to respond omni-directionally to a radio excitation and to emit a signature radio signal in response to excitation. RFID structures, for example, may be integrated into (or attached to) the tools. Similar radiobeacons may be integrated into (or attached to) prostheses, and as described above, may also be integrated into or inserted under the surgeon's gloves.

Also shown is an operating table 2610 that may serve as a stable coordinate reference frame for the headset. Four radiobeacons may be placed at the corners of the table so as to reflect radio signatures back to a triplet array of radio receivers in the headset. Simple triangulation algorithms permit a computing machine to calculate headset position from time of flight measurements performed with a high frequency clock. Frequencies of 5.5 MHz or higher may be used to improve the accuracy of the positional sensing.

Advantageously, the radiobeacons may also be placed at the corners of a Mayo table, a slip-on cover on the Mayo table, the corners of the operating table, or a mat under the surgeon's feet, each corner having a radio reflective antenna equipped with an identifiable signature reflection. In this way, the headset orientation may be tracked by an external reference frame, but one that is not subject to the weaknesses of optical tracking. The surgeon may calibrate the system by pointing out at least one beacon associated with a boney prominence or obvious anatomical feature that is present on the wireframe map, and the internal solid model and the rest of the beacons can then be formed into a spatial map that is determinate and inflexible for the duration of the procedure. If the patient is rolled over, for example, only one or two beacons may be disturbed, so their positions may be refreshed while the remaining beacons are fixed in a master coordinate array stored in computer memory. Tracking the headset may be relatively easy using standard matrix algebra and may require substantially less computational power.

At least one computer/server may be connected to the headset, generally by a data umbilicus as shown in FIG. 2. The umbilicus may also route fiber optics to the headset dot matrix projector. The computer/server may include client software routines and memory sufficient to handle and store image-related digital databases.

The following is a partial list of software engines that may be used in the surgical navigation systems: a subroutine for constructing a wireframe model of a surgical field and roughing in relative viewpoint of a headset; a subroutine for creating a 3D model from tomographical datasets; a subroutine for administering a data library of 3D models, including tools; a subroutine for registering the 3D model with the actual patient; a subroutine for "segmenting" anatomy (splitting an image into its component body elements and treating each body element separately in the model); a subroutine for tracking tools; a subroutine for tracking an eyeball of an unaided eye; a subroutine for tracking a surgeon's hands (likely with special gloves); a subroutine for image analysis, including geometry on segmented anatomical elements; a subroutine for handling voice commands; and a subroutine for dynamic raytrace of virtual display elements with perspective (dynamic indicating updating at a frame rate of at least 30 fps, or in real-time).

Reflections of structured or unstructured light dots may be used to track the surgical field and anatomical landmarks (no retroreflective ball apparatus is used) and reflections of VIS dots (here indicating a blue, violet or ultraviolet dot matrix) may be used to track the hands and tools. The radiobeacons may be coarse navigational aids for roughing in the position of tools and a permanent reference on the outside boundary of the surgical field (so as to size the area where fine mapping is needed and to speed up the recapture of the correct orientation frame when the visual image is interrupted). By using two dot systems that are superimposed, the gloves can be subtracted from the surgical view or vice versa, and blocking can be selectively used to better reinforce the illusion of stereopsis without a binary eye system. Alternatively, body and most relevant bones or anatomical targets can be displayed as a solid and hands or tools can be displayed as a ghost image, or vice versa. Tools may be displayed without the hands supporting them so as to minimize obstruction of the surgical field. Tools may also be provided with analytics, including angle and guidepath projections.

Also a component in the system is "wetware" which the operating surgeon is proficient in using. The inputs to the wetware are optimized to avoid fatigue and to prevent confusion and defects in hand-eye coordination that could result from misaligned virtual augmentation. A functional corpus callosum and optic chiasma are needed to interpret the unaided eye view in conjunction with the augmented views in the eyepiece. This is referred to as "wetware". So the system may be interpreted to have a software component, a hardware component, and a wetware component. Generally one unaided eye is used and the augmented eye is provided with an eyepiece for receiving virtually enhanced images and data feeds such as text. Voice commands and haptic gestures may be used to control the virtual display and may be used to turn off a view of one or the other hand, for example, so as to disable ambiguous visual cues such as an anatomical view superimposed on top of the surgeon's arm or wrist. When used in combination with a segmented library of anatomical parts, tools and prosthetics, the capacity to also segment the surgeon's hands offer multiple advantages in reducing image clutter, improving depth cues, and directing computing operations without interference from background noise and without the need for remote control interfaces. Advantageously, segmentation also permits presentation of anatomical views with reduced complexity and clutter, limiting the view to the more relevant structures. This again reduces inappropriate superimposing of images and simplifies the computational process.

Figure 27:
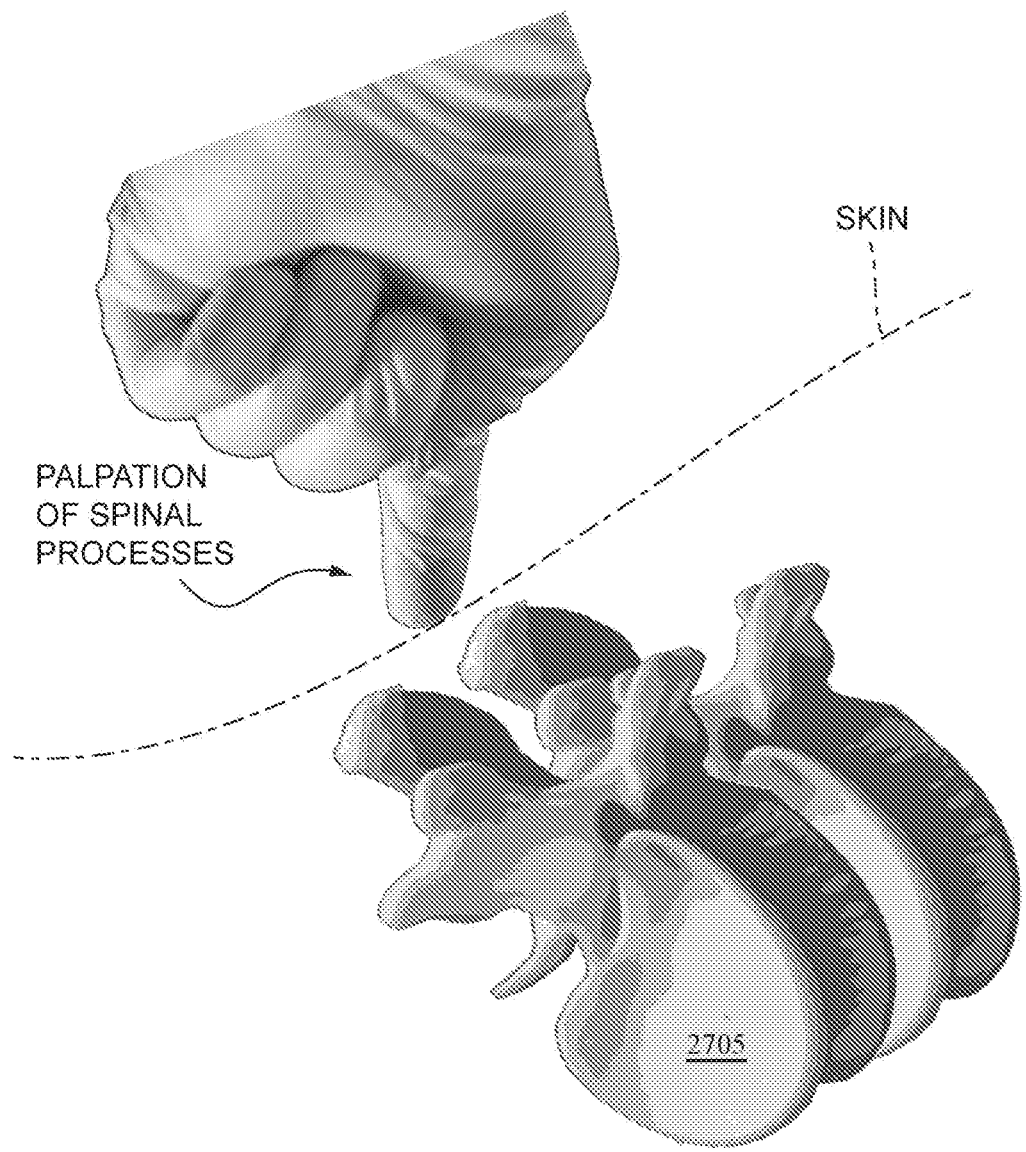
FIG. 27 shows an example headset view of multiple virtual objects by which at least aspects of surgical navigation may be implemented.

FIG. 27 shows an example headset view 2700 of multiple virtual objects by which at least aspects of surgical navigation may be implemented, arranged in accordance with at least some embodiments described herein. For example, while one vertebra is shown in FIGS. 25B and 25C, multiple bone clusters 2705 may also be manipulated where surgically relevant, as shown in FIG. 27. A display of all the vertebra would result in visual clutter, but showing two contacting vertebrae may be relevant to a range of spinal surgeries, such as discectomy. A segmented image library is utilized in this example, and FIG. 27 illustrates how information relevant to the surgical procedure may be presented with clarity by elimination of unwanted elements such as ribs and uninvolved vertebrae. This image may also be less computationally dense and can be more rapidly updated as the surgeon's view changes. In this example, the surgeon may be looking through the thorax and views the ventral aspect of the spinal cord while pointing to particular vertebra with a pair of surgical gloves that are visible in the unaided eye and are used in virtual space to select the anatomy of interest. Here, finger pointing may be used to pick out two vertebrae having a normal joint space. As described above, further manipulation of the image may result in a streaming display providing quantitative measurement of the disc thickness. Soft tissue views may also be superimposed if desired and the image may be accompanied by nerve transmission studies or sections showing myelographs if available.

The surgeon's fingertip may also trace the spine to identify spinous processes. This method of identifying anatomical landmarks is termed "palpation", and may be digitally enhanced as described below.

Figure 28A:
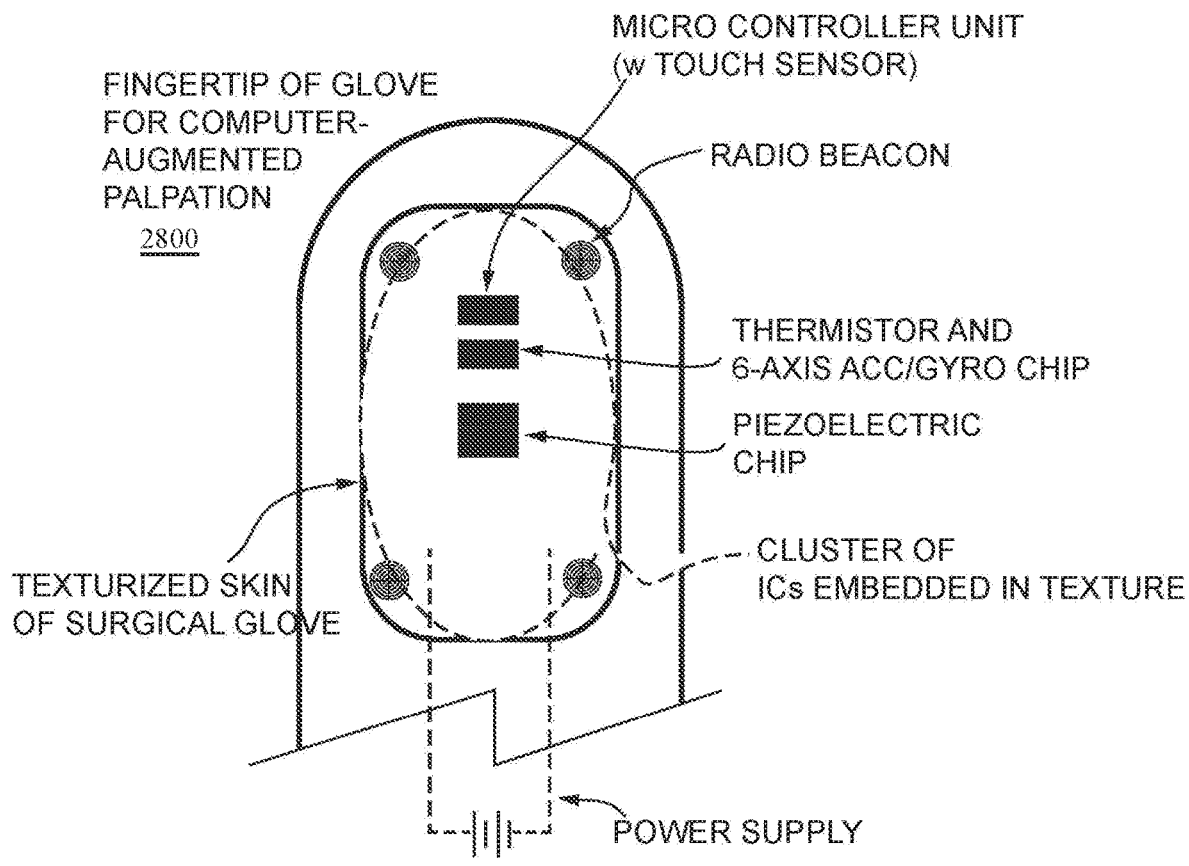
FIGS. 28A and 28B show a schematic representation of an example fingertip portion of a surgical glove by which at least aspects of surgical navigation may be implemented.
Figure 28B:
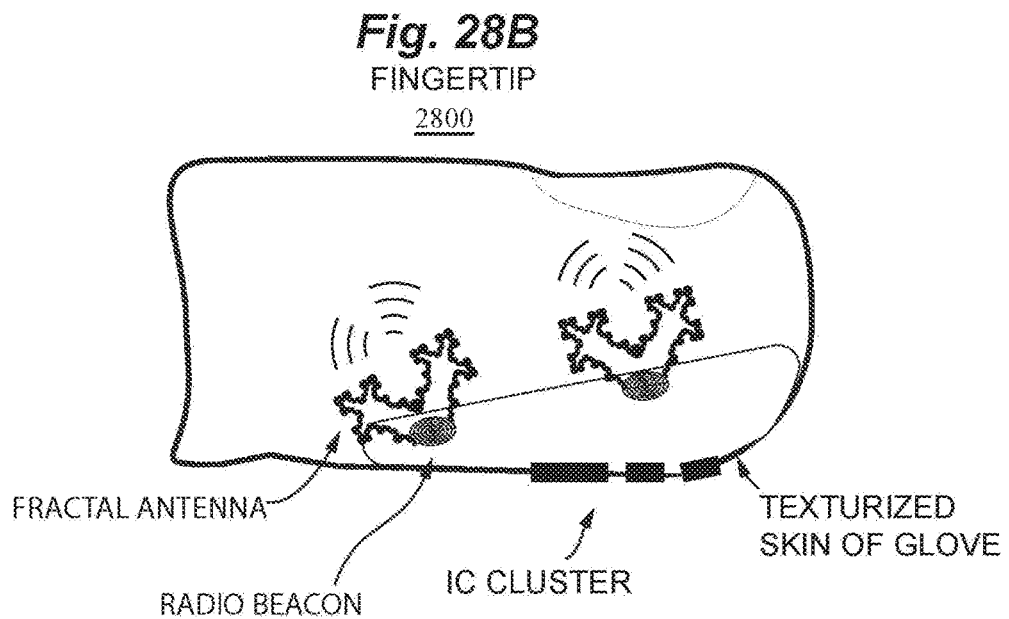

FIGS. 28A and 28B show a schematic representation of an example fingertip portion 2800 of a surgical glove by which at least aspects of surgical navigation may be implemented, arranged in accordance with at least some embodiments described herein. In this example, surgical gloves may be modified to include a cluster of IC chips and supporting circuitry as needed to sense touch. Computer-augmented palpation may be achieved by combining a cluster or at least one radiobeacon in a fingertip so that location may be tracked and one or more ICs for special functions. Shown here by way of example is an MCU ARM chip for digitizing the sensation of touch, four radiobeacons, a 6-axis accelerator/gyroscope and magnetometer integrated circuit with thermistor, and a piezoelectric chip for delivering ultrasound when contacted with a substrate such as skin.

FIG. 28B shows an example side view of the IC cluster and radiobeacons with fractal antennas. Other antenna configurations, such as dielectric or ceramic microstrip antennas and dipole antennas, while not limited thereto, may be used to limit the size and complexity of the antenna structure.

Figure 29:
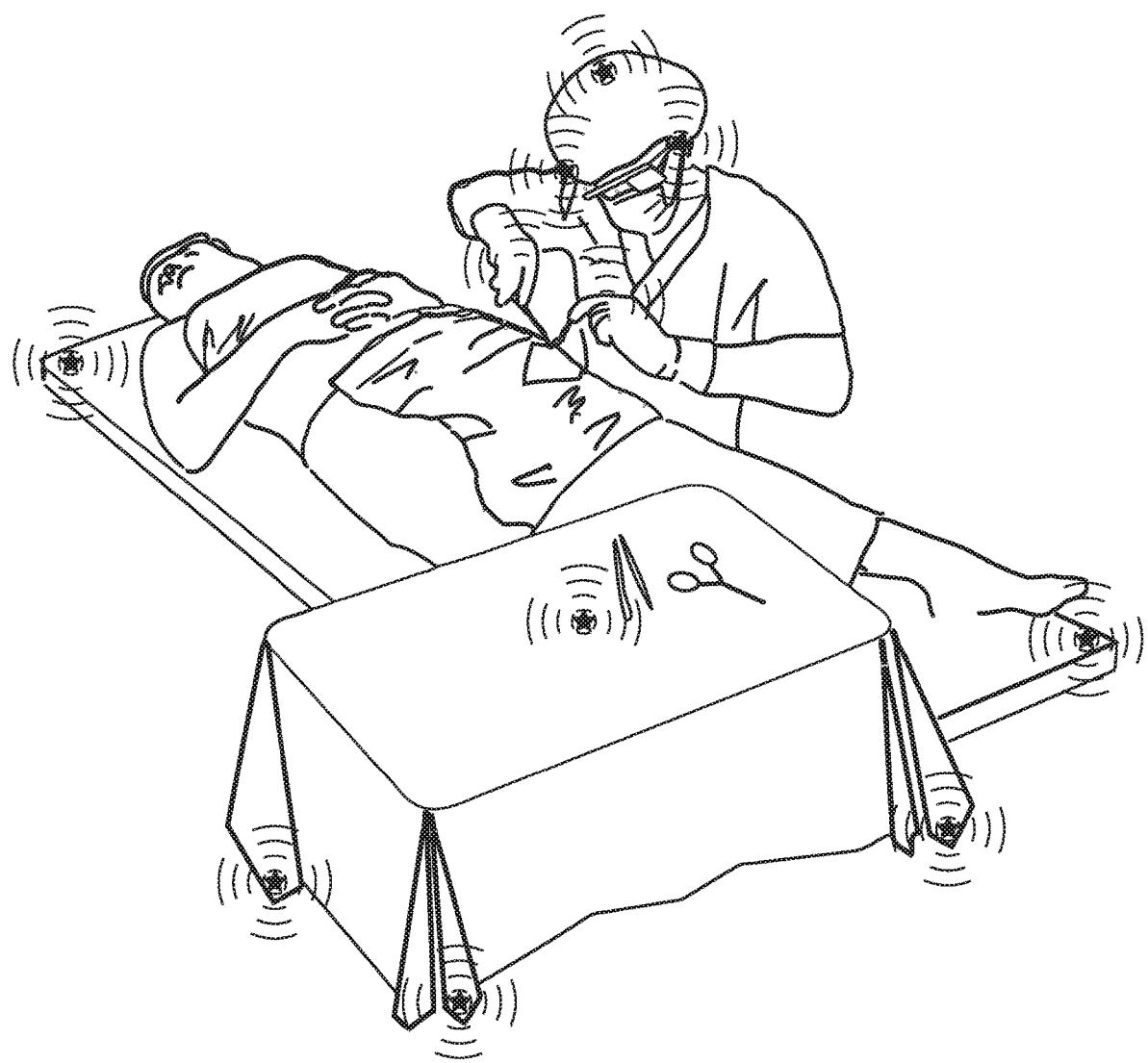
FIG. 29 shows an example radiobeacon reference coordinate frame and headset by which at least aspects of surgical navigation may be implemented, all arranged in accordance with at least some embodiments described herein.

FIG. 29 shows an example radiobeacon reference coordinate frame and headset by which at least aspects of surgical navigation may be implemented, arranged in accordance with at least some embodiments described herein. In this example, the radiobeacon reference coordinate frame and eyewear are configured to project views of the internal anatomy and data to the surgeon's left eye. The reference coordinate frame may be used to fuse larger 3D anatomical images such as a CT model to points designated by the surgeon. In this more field-like operating theater, the surgeon may drag and drop the CT model into the correct anatomy using a pre-haptic set of gestures and haptic features built into the gloves. This may be achieved without a dotted light projector and may include at least one radiobeacon mounted in each of a pair of surgical gloves and a plurality of radio receivers mounted in association with headgear worn by the surgeon, the radio receivers functioning to perform triangulation on the radiobeacons dispersed in the surgical napkin on the Mayo table and on the corners of the gurney. These may provide the foundational reference coordinate system used to present optically realistic augmented reality displays in the eyepiece.

In a simplified method, radiobeacons may be used as the primary reference frame for data fusion with more complex datasets. The eyepiece may display virtual views in a correct anatomical orientation as seen by the surgeon and move the perspective as the surgeon moves. In this example, a radiobeacon reference frame may be used as a foundation for augmented reality presented via a surgical eyepiece, heads-up display, or pseudo-holographic view.

As noted above, radiobeacons may be used to create reference frames for fusion of spatial 3D datasets with patient anatomy as visible to a surgeon in alternation with or to complement with an optical scanning system. By correlating a 3D model with a reference frame and associating that reference frame with an accurate positioning of the patient, the 3D model may be projected as a virtual image into an eyepiece of a headset such that the 3D model is closely aligned with the actual anatomy. The working example is that of a CT dataset, which when superimposed in a virtual view on the patient, reveals underlying boney anatomy not directly visible to the surgeon prior to dissection. The basic reference coordinate frame may be provided by a set of radiobeacons disposed in the operating theater.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

I claim:

1. A computer-readable medium having computer-executable instructions stored thereon that, when executed, cause one or more processors to:
    direct a dot matrix array of non-visible light beams from a projector onto a surgical site, wherein the dot matrix array is dynamically adaptive and encoded;
    produce optical data regarding the surgical site based on light reflected from the surgical site and collected by a camera mounted to a user's headset;
    receive user instructions to direct an optical pointer towards physical reference landmarks on physical anatomical reference features of a patient;
    construct a three-dimensional model based on the optical data;
    produce mapping points by associating annotations provided as the optical pointer lights up the respective physical reference landmarks, wherein the mapping points stabilize images to smooth real-time scanning as the user's headset is moved;
    receive user instructions to highlight and inspect respective ones of the anatomical reference features based on the reference landmarks; and
    inspect the three-dimensional model of the highlighted anatomical reference features according to received user instructions.

2. The computer-readable medium of claim 1, wherein the computer-executable instructions further cause the one or more processors to:
    fuse the constructed three-dimensional model with an internal three-dimensional model of the surgical site from the viewpoint of the headset, wherein the internal three-dimensional model is derived from a medical imaging process;
    register the internal three-dimensional model with the mapping points;
    generate an aligned view of the surgical site;
    provide the aligned view of the surgical site to the headset; and
    update the aligned view of the surgical site in real-time using the mapping points.

3. The computer-readable medium of claim 2, wherein the updated aligned view of the surgical site is viewable at an unaligned view for the user.

4. The computer-readable medium of claim 1, wherein the instructions to inspect the anatomical reference features include an instruction to rotate the three-dimensional model of the highlighted anatomical reference features.

5. The computer-readable medium of claim 1, wherein the instructions to inspect the anatomical reference features include an instruction to divide the three-dimensional model of the highlighted anatomical reference features.

6. The computer-readable medium of claim 1, wherein the instructions to inspect the anatomical reference features include an instruction to enlarge the size of the three-dimensional model of the highlighted anatomical reference features.

7. The computer-readable medium of claim 1, wherein the user instructions to inspect the anatomical reference features are received from surgical gloves, worn by the user, having RFID chips inserted therein.

8. The computer-readable medium of claim 7, wherein the user instructions received from the surgical gloves are based on thumb and forefinger gestures made by the user.

9. The computer-readable medium of claim 1, wherein the highlighted anatomical reference features include implants for which measurements are stored and retrievable from memory.

10. A computer-readable medium having computer-executable instructions stored thereon that, when executed, cause one or more processors to:
    direct a dot matrix array of non-visible light beams from a projector onto a surgical site, wherein the dot matrix array is dynamically adaptive and encoded;
    produce optical data regarding the surgical site based on light reflected from the surgical site and collected by a camera mounted to a user's headset;
    receive user instructions to direct an optical pointer towards physical reference landmarks on physical anatomical reference features of a patient;
    construct a three-dimensional model based on the optical data and radio signals, wherein the radio signals are generated from radio beacons; and
    produce mapping points by associating annotations provided as the optical pointer lights up the respective physical reference landmarks, wherein the mapping points stabilize images to smooth real-time scanning as the user's headset is moved.

11. The computer-readable medium of claim 10, wherein the instructions direct a dot matrix array of non-visible light beams from a projector mounted to a headset onto a surgical site.

* * * * *